United States Patent
Kocis et al.

(10) Patent No.: US 12,285,400 B2
(45) Date of Patent: Apr. 29, 2025

(54) SULFOPROPANOIC ACID DERIVATIVES FOR TREATING NEURODEGENERATIVE DISORDERS

(71) Applicant: Alzheon, Inc., Framingham, MA (US)

(72) Inventors: Petr Kocis, Framingham, MA (US); John Hey, Framingham, MA (US); Martin Tolar, Framingham, MA (US)

(73) Assignee: Alzheon, Inc., Framingham, MA (US)

( * ) Notice: Subject to any disclaimer, the term of this patent is extended or adjusted under 35 U.S.C. 154(b) by 919 days.

(21) Appl. No.: 17/264,478

(22) PCT Filed: Jul. 30, 2019

(86) PCT No.: PCT/US2019/044114
§ 371 (c)(1),
(2) Date: Jan. 29, 2021

(87) PCT Pub. No.: WO2020/028348
PCT Pub. Date: Feb. 6, 2020

(65) Prior Publication Data
US 2022/0087967 A1    Mar. 24, 2022

Related U.S. Application Data

(60) Provisional application No. 62/713,056, filed on Aug. 1, 2018.

(51) Int. Cl.
*A61K 31/221* (2006.01)
*A61K 31/185* (2006.01)
(Continued)

(52) U.S. Cl.
CPC .......... *A61K 31/221* (2013.01); *A61K 31/185* (2013.01); *A61K 31/22* (2013.01); *A61P 25/28* (2018.01)

(58) Field of Classification Search
CPC ...... A61K 31/221; A61K 31/185; A61P 25/28
See application file for complete search history.

(56) References Cited

FOREIGN PATENT DOCUMENTS

| CN | 1753675 A | 3/2006 |
|---|---|---|
| CN | 106170563 A | 11/2016 |

(Continued)

OTHER PUBLICATIONS

Kocis P, Tolar M, Yu J, Sinko W, Ray S, Blennow K, Fillit H, Hey JA. Elucidating the Aβ42 Anti-Aggregation Mechanism of Action of Tramiprosate in Alzheimer's Disease: Integrating Molecular Analytical Methods, Pharmacokinetic and Clinical Data. CNS Drugs. Jun. 2017;31(6):495-509. (Year: 2017).*

(Continued)

*Primary Examiner* — Clinton A Brooks
*Assistant Examiner* — Josmalen M. Ramos-Lewis
(74) *Attorney, Agent, or Firm* — McCarter & English, LLP; Michael J. DeGrazia

(57) ABSTRACT

Provided herein is the use of a compound of Formula (I):

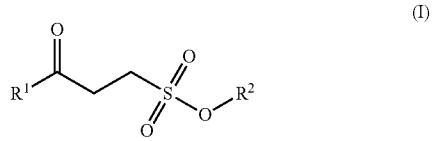

or a pharmaceutically acceptable salt thereof, for treating a disease characterized by amyloid and amyloid-like aggregates, e.g., Alzheimer's disease.

16 Claims, 10 Drawing Sheets

(51) Int. Cl.
*A61K 31/22* (2006.01)
*A61P 25/28* (2006.01)

(56) References Cited

FOREIGN PATENT DOCUMENTS

| CN | 108289870 A | 7/2018 | | |
|---|---|---|---|---|
| JP | 11-501635 A | 2/1999 | | |
| WO | 1996/28187 A1 | 9/1996 | | |
| WO | WO 1996028187 A1 * | 9/1996 | ............. | A61K 47/48 |
| WO | WO-2007063428 A2 * | 6/2007 | ............. | A61K 31/19 |
| WO | 2017/044840 A1 | 3/2017 | | |
| WO | 2020/028348 A1 | 2/2020 | | |

OTHER PUBLICATIONS

Hey JA, Yu JY, Versavel M, Abushakra S, Kocis P, Power A, Kaplan PL, Amedio J, Tolar M. Clinical Pharmacokinetics and Safety of ALZ-801, a Novel Prodrug of Tramiprosate in Development for the Treatment of Alzheimer's Disease. Clin Pharmacokinet. Mar. 2018;57(3):315-333 Published Online 2017. (Year: 2018).*

Hey JA, Kocis P, Hort J, Abushakra S, Power A, Vyhnálek M, Yu JY, Tolar M. Discovery and Identification of an Endogenous Metabolite of Tramiprosate and Its Prodrug ALZ-801 that Inhibits Beta Amyloid Oligomer Formation in the Human Brain. CNS Drugs. Sep. 2018;32(9):849-861. (Year: 2018).*

Placzek, A. T., Ferrara, S. J., Hartley, M. D., Sanford-Crane, H., Meinig, J. M., & Scanlan, T. S. (2016). Sobetirome prodrug esters with enhanced blood-brain barrier permeability. Bioorganic & Medicinal Chemistry, 24(22), 5842-5854. (Year: 2016).*

S. Abushakra ; M. Tolar , et al., (2016): Clinical Benefits of Tramiprosate in Alzheimer's Disease Are Associated with Higher Number of APOE4 Alleles: The "APOE4 Gene-Dose Effect". The Journal of Prevention of Alzheimer's Disease (JPAD). http://dx.doi.org/10.14283/jpad.2016.115 (Year: 2016).*

Kocis, P., Hey, J. A., Abushakra, S., Power, A., & Tolar, M. (Jun. 2, 2017). Insights to support a new class of therapeutics in Alzheimer's disease. Drug Target Review. https://www.drugtargetreview.com/article/23683/therapeutics-alzheimers-disease/ (Year: 2017).*

Demetre, D. C. (Aug. 6, 2018). 3-SPA: Endogenous substance inhibits formation of beta amyloid oligomers—ScienceBeta. ScienceBeta. https://sciencebeta.com/3spa-amyloid-oligomers/ (Year: 2018).*

Abushakra S, Clinical Benefits of Tramiprosate in Alzheimer's Disease Are Associated with Higher No. of APOE4 Alleles: The "APOE4 Gene-Dose Effect". J Prev Alzheimers Dis. 2016;3(4):219-228. (Year: 2016).*

Abushakra et al., Clinical Benefits of Tramiprosate in Alzheimer's Disease Are Associated with Higher Number of APOE4 Alleles: The "APOE4 Gene-Dose Effect". J Prev Alzheimers Dis. 2016;3(4):219-228.

Hey et al., Clinical Pharmacokinetics and Safety of ALZ-801, a Novel Prodrug of Tramiprosate in Development for the Treatment of Alzheimer's Disease. Clin Pharmacokinet. Mar. 2018;57(3):315-333.

Hey et al., Discovery and Identification of an Endogenous Metabolite of Tramiprosate and Its Prodrug ALZ-801 that Inhibits Beta Amyloid Oligomer Formation in the Human Brain. CNS Drugs. Sep. 2018;32(9):849-861.

* cited by examiner

SULFOPROPANOIC ACID DERIVATIVES FOR TREATING NEURODEGENERATIVE DISORDERS

RELATED APPLICATIONS

RELATED APPLICATIONS

This application is a 35 U.S.C. § 371 national stage filing of International Application No. PCT/US2019/044114, filed on Jul. 30, 2019, which claims priority to U.S. Provisional Application No. 62/713,056, filed Aug. 1, 2018, the entire contents of each of which are incorporated herein by reference.

BACKGROUND

Alzheimer's disease (AD) is a progressive degenerative disease of the brain primarily associated with aging. The growing magnitude of the health care cost to society for AD is underscored by the number of patients afflicted across geographical regions with over 5.7 million in the U.S. (Alzheimer's Association 2018) and 35 million worldwide (World Alzheimer Report 2016). Clinical presentation of AD is characterized by loss of memory, cognition, reasoning, judgment, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Presently, the two classes of approved drugs for AD are cholinesterase inhibitors and memantine. Both classes are symptomatic agents that target secondary neurotransmitter deficiencies seen in AD. Neither class, however, demonstrates efficacy beyond 6 months of treatment in clinical trials and there is no evidence of these classes targeting the underlying disease pathology. Emerging anti-amyloid antibodies (e.g. aducanumab) show promise as potential disease-modifying treatments when used at early stages of the disease. See e.g., Lasser et al. Efficacy and Safety of Gantenerumab in Prodromal AD: Results from Scarlet Road—a Global, Multicenter Trial. Alzheimer's Association International Conference (AAIC) 2015 Abstract ID: 5963. However, some amyloid immunotherapies have been associated with a dose-dependent risk of amyloid related imaging abnormalities with edema (ARIA-E), with increased risk reported in APOE4 carriers. See e.g., Salloway et al. Two Phase 3 Trials of Bapineuzumab in Mild-to-Moderate Alzheimer's Disease. N Engl J Med 2014; 370:322-33; Sevigny et al., The antibody aducanumab reduces Abeta plaques in Alzheimer's disease. Nature 2016; 537:50-6; and Caselli et al. Longitudinal modeling of age-related memory decline and the APOE epsilon4 effect. N Engl J Med 2009; 361:255-263. This presents a development challenge, since doses that show amyloid clearance and clinical benefit are associated with approximately 40% incidence of ARIA-E at the two highest doses of aducanumab. See Sevigny et al. A dose titration regimen with aducanumab still shows approximately 35% incidence of ARIA-E in APOE carriers. See e.g., Viglietta et al., Aducanumab titration dosing regimen: 12-month interim analysis from prime, a randomized double blind, placebo-controlled phase Ib study in patients with prodromal or mild Alzheimer's disease. J Prev Alzheimers Dis 2016; 3, suppl 1:378. Although ARIA-E may be asymptomatic or mildly symptomatic in most patients, some patients may develop seizures or other serious adverse events. The risk of ARIA-E in AD patients may require MRI monitoring, which is burdensome in elderly population, and could limit the utility of these drugs in clinical practice.

Soluble low molecular weight $A\beta 42$ oligomers are now recognized as key drivers of AD pathogenesis and increased concentration of $A\beta 42$ oligomers correlates closely with onset and progression of clinical symptoms. See e.g., Viglietta et al. Soluble $A\beta$ oligomers have been shown to cause synaptic damage, neuronal death, promote tau phosphorylation and drive tau pathology. See e.g., Esparza et al., Amyolid beta oligomerization in Alzheimer's dementia vs. high pathology controls. Ann Neurol 2013; 73(1):104-119; Hashimoto et al. Apolipoprotein E, especially apolipoprotein E4, increases t peptide. J Neurosci. 2012; 32:15181-15192; Ono et al., Low-n oligomers as therapeutic targets of Alzheimer's disease. J. Neurochem. 2011; 117:19-28; Townsend et al., Effects of secreted oligomers of amyloid beta-protein on hippocampal synaptic plasticity: a potent role for trimers. J. Physiol.; 2006; 572:477-92; and Lambert et al. Diffusible, nonfibrillar ligands derived from A 1-42 are potent central nervous system neurotoxins. PNAS. 1998; 95:6448-53. Importantly, APOE 4/4 AD patients have been shown to a have a higher burden of soluble amyloid oligomers (Usui et al., Site-specific modification of Alzheimer's peptides by cholesterol oxidation products enhances aggregation energetics and neurotoxicity. PNAS.; 2009; 106:18563-8), which is likely responsible for the earlier disease onset in this population.

To date, only agents targeting $A\beta$ oligomers such as aducanumab and ALZ-801/tramiprosate have shown clinical benefits in amyloid positive AD patients. Tramiprosate, 3-amino-1-propanesulfonic acid (SAPS) is an oral amyloid anti-aggregation agent which reduces amyloid beta oligomer neurotoxicity. The tramiprosate Phase 3 trials in mild-to-moderate AD showed an excellent drug profile, including the capability to slow the reduction of brain hippocampal volume, and to improve brain cognition and function in subset analyses. See e.g., Gauthier, S. et al. Effect of tramiprosate in patients with mild-to-moderate Alzheimer's disease: exploratory analyses of the MRI sub-group of the Alphase study. J Nutr Health Aging 13, 550-557 (2009); Saumier, D., Duong, A., Haine, D., Garceau, D. & Sampalis, J. Domain-specific cognitive effects of tramiprosate in patients with mild to moderate Alzheimer's disease: ADAS-cog subscale results from the Alphase Study. J Nutr Health Aging 13, 808-812 (2009); and Aisen, P. S. et al. Tramiprosate in mild-to-moderate Alzheimer's disease—a randomized, double-blind, placebo-controlled, multi-centre study (the Alphase Study). Arch Med Sci 7, 102-111 (2011).

ALZ-801 is in clinical development as an oral, small molecule inhibitor of beta amyloid ($A\beta$) oligomer formation for the treatment of Alzheimer's disease (AD). ALZ-801 is a valine conjugate of tramiprosate with improved pharmacokinetic properties and gastrointestinal tolerability. See e.g., Hey et al., Clinical Pharmacokinetics and Safety of ALZ-801, a Novel Prodrug of Tramiprosate in Development for the Treatment of Alzheimer's Disease. Clin Pharmacokinetics 2018; 315-333. Tramiprosate, the active moiety of ALZ-801, inhibits the formation of $A\beta$ oligomers in vitro. See e.g., Kocis et al., Elucidating the Abeta42 Anti-Aggregation Mechanism of Action of Tramiprosate in Alzheimer's Disease: Integrating Molecular Analytical Methods. Pharmacokinetic and Clinical Data. CNS Drugs 2017; 31:495-509. Oral tramiprosate was previously evaluated in two Phase 3 studies, which included 2,015 patients with mild to moderate AD, treated with 100 mg BID of tramiprosate, 150 mg BID of tramiprosate, or placebo. Safety data from these Phase 3 trials and the safety extension study, suggest a favorable safety profile with tramiprosate exposures of up to 2.5 years. See e.g., Abushakra et al., Clinical effects of tramiprosate in APOE 4/4 homozygous patients with mild Alzheimer's disease suggest disease modification potential. J Prev Alzheimers Dis 2017; 4:149-56. In a subgroup analysis of subjects with the ε4 allele of apolipoprotein E (APOE4), there was a positive and clinically meaningful benefit on cognition.

SUMMARY

The biotransformation of ALZ-801 to tramiprosate is shown in FIG. 1. As explained earlier, tramiprosate inhibits the formation of Aβ oligomers and is being evaluated for the treatment of mild to moderate AD.

We have now found a metabolite of tramiprosate, 3-sulfopropanoic acid (3-SPA), present in human cerebrospinal fluid (CSF) and plasma of drug-naïve subjects (See e.g., FIG. 2 and FIG. 3), and have identified that this metabolite inhibits aggregation of Aβ42 into small oligomers with efficacy comparable to that of tramiprosate itself. See e.g., FIG. 4 and FIG. 5.

In addition, we identified an inverse correlation between cognitive impairment severity and the concentration of 3-SPA in subjects having mild to moderate AD, therefore suggesting that the level of 3-SPA diminishes as the severity of the cognitive impairment increases and that maintaining higher levels of 3-SPA may play a role in preventing or diminishing the cognitive decline associated with AD, for example as measured by a subject's Mini Mental State Examination ("MMSE") score, a well-documented method for determining the severity of Alzheimer's Disease in the subject. See e.g., Pangman, et al., Applied Nursing Research. 13 (4): 209-213. What we found was that AD subjects with a higher MMSE score (i.e., less cognitive impairment) possessed higher levels of 3-SPA in the CSF when compared to subjects with lower MMSE scores. See e.g., FIG. 6. This correlation allowed us to determine the trend, or line of best fit, between MMSE score and 3-SPA concentration in CSF for subjects in the test population who were suffering from mild to moderate AD.

From these findings, we hypothesize that increasing 3-SPA CSF levels, e.g., to above those found in AD subjects with the least cognitive impairment (i.e., MMSE=30) (a "baseline threshold level") and maintaining such elevated levels should protect those subjects from further cognitive decline or reduce the rate of cognitive decline as compared to a placebo treatment. Increasing 3-SPA CSF levels to above such baseline threshold level can be achieved by administering ALZ-801, tramiprosate, or a precursor thereof (all of which ultimately produce 3-SPA), or by administering an exogenous form of 3-SPA directly.

Provided herein, therefore, are compounds which are designed to metabolize to 3-SPA, and therefore increase 3-SPA CSF levels to those subjects in need of protection, e.g., subjects suffering from Alzheimer's disease, dementia, or cognitive decline. The compounds described herein include compounds having the Formula I:

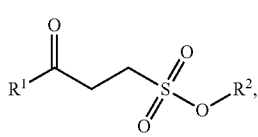

(I)

or a pharmaceutically acceptable salt thereof.

Also provided herein are methods for using the disclosed compounds to treat Alzheimer's disease (AD) in subjects having a 3-SPA concentration below a certain baseline threshold level e.g., below the 3-SPA CSF concentration (±10%) value determined for a MMSE of 30 in a best fit of a random population of subjects with AD of varying cognitive impairment Also provided herein are methods for treating selected AD subjects defined by various severities of cognitive impairment. For example, in one aspect, the selected subjects for treatment may have certain MMSE scores indicating, for example, an AD severity of mild or mild to moderate. In other aspects, subjects may have certain MMSE scores and have one or more of the ε4 allele of the apolipoprotein E (APOE) gene (e.g., be homozygous for APOE4), an abnormal Free and Cued Selective Reminding (FCSR) memory test indicating mild cognitive impairment, and a certain clinical dementia rating (CDR).

Further provided herein are methods for preventing dementia or preventing further cognitive decline in subjects having a 3-SPA concentration below a certain baseline threshold level e.g., below the 3-SPA CSF concentration (±10%) value determined for a MMSE of 30 in a best fit of a random population of subjects suffering from cognitive decline.

BRIEF DESCRIPTION OF THE FIGURES

FIG. 8 Panel B represents the LC-MS/MS chromatograms for human CSF from a single AD subject with MMSE 20.

DETAILED DESCRIPTION

1. Definitions

Figure 1:
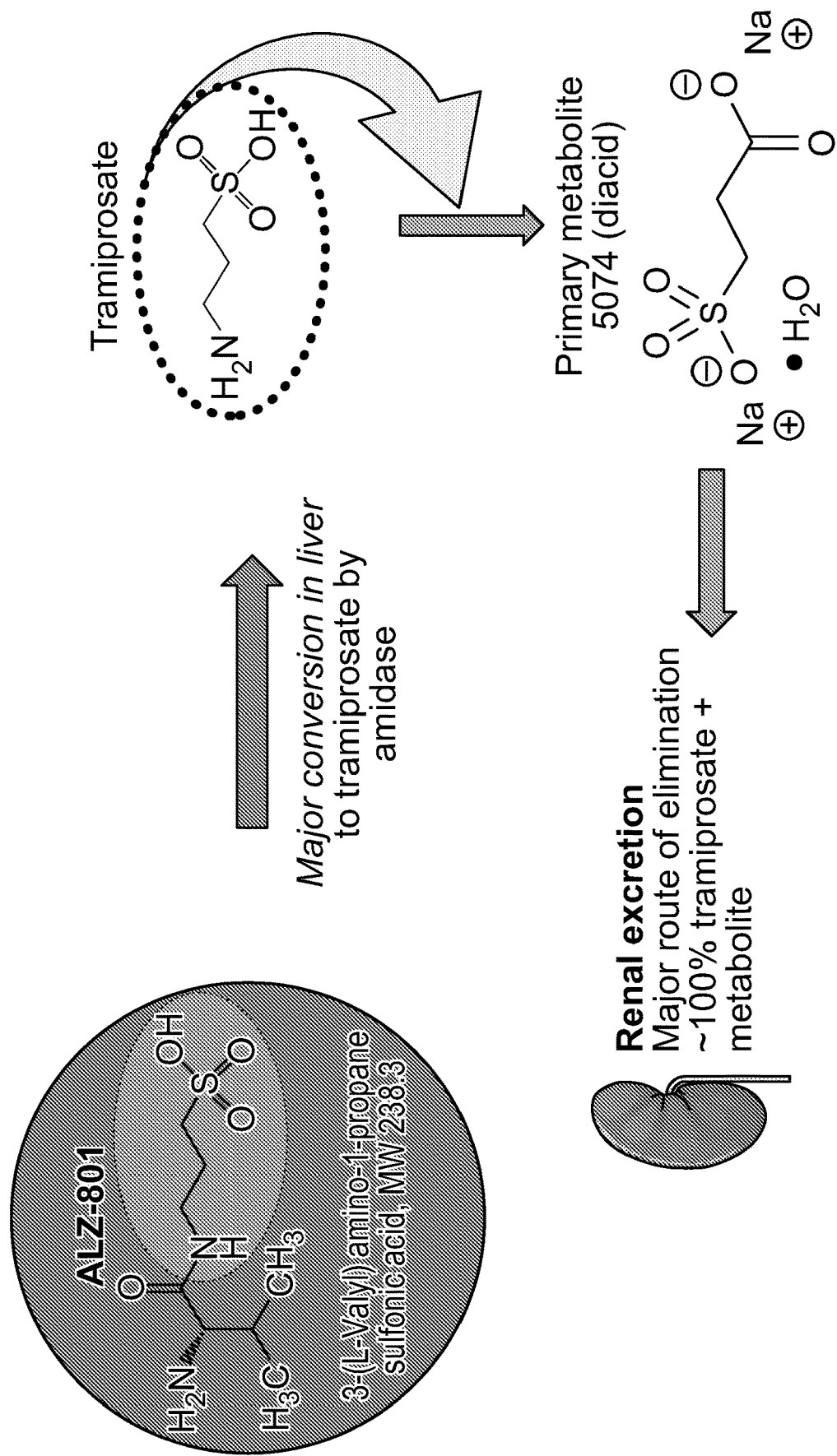
FIG. 1 illustrates the metabolic transformation of ALZ-801 to 3-sulfopropanoic acid (3-SPA).

As used herein, a hyphen ("-") at the beginning or end of a recited group designates the point at which a recited group is attached to a defined group. For example, —O—($C_1$-$C_4$ alkyl) means that the group is attached via the oxygen atom.

The term "alkylene" refers to a straight or branched bivalent alkyl group.

The term "$C_0$ alkylene" as used herein means a bond. Thus, a moiety defined herein as "—($C_0$-$C_{20}$ alkylene)-aryl" includes both -aryl (i.e., $C_0$ alkylene-aryl) and —($C_1$-$C_{20}$ alkylene)-aryl.

The term "alkenylene" refers to a straight or branched bivalent alkenyl group.

The term "alkynylene" refers to a straight or branched bivalent alkynyl group.

The term "alkyl", used alone or as a part of a larger moiety such as e.g., "haloalkyl", means a saturated monovalent straight or branched hydrocarbon group having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkenyl", used alone or as a part of a larger moiety such as e.g., "haloalkenyl", means a monovalent group derived from a straight- or branched-chain aliphatic moiety having at least one carbon-carbon double bond having, unless otherwise specified 1-10 carbon atoms. Representative alkenyl groups include, but are not limited to, ethenyl ("vinyl"), propenyl ("allyl"), butenyl, 1-methyl-2-buten-1-yl, and the like.

The term "alkynyl", used alone or as a part of a larger moiety such as e.g., "haloalkynyl", means a monovalent group derived from a straight- or branched-chain aliphatic moiety having at least one carbon-carbon triple bond having, unless otherwise specified 1-10 carbon atoms. Representative alkynyl groups include, but are not limited to, ethynyl, 2-propynyl ("propargyl"), 1-propynyl, and the like.

"Alkoxy" is an alkyl group which is attached to another moiety via an oxygen linker (—O(alkyl)). Non-limiting examples include methoxy, ethoxy, propoxy, and butoxy.

The terms "halo" and "halogen" as used herein refer to an atom selected from fluorine (fluoro, —F), chlorine (chloro, —Cl), bromine (bromo, —Br), and iodine (iodo, —I).

The term "carbocyclyl" (also referred to herein as "carbocycle" "cycloaliphatic" or "cycloalkyl"), as used herein, means a monocyclic hydrocarbon or bicyclic hydrocarbon, wherein each ring is completely saturated or partially saturated, but not aromatic.

The term "aryl" used alone or as part of a larger moiety as in "aralkyl", "aralkoxy", or "aryloxyalkyl", refers monocyclic and bicyclic carbon ring system having a total of five to 10 ring members, wherein at least one ring in the system is aromatic. The term "aryl" may be used interchangeably with the term "aryl ring". In certain embodiments, "aryl" refers to an aromatic ring system which includes, but not limited to, phenyl, biphenyl, naphthyl, anthracyl and the like. In one embodiment, "aryl" is phenyl. It will be understood that when specified, optional substituents on an aryl group may be present on any substitutable position.

The term "heteroaryl" used alone or as part of a larger moiety as in "heteroarylalkyl", "heteroarylalkoxy", or "heteroarylaminoalkyl", refers to a 5- to 12-membered, fully aromatic ring system containing 1-4 heteroatoms selected from N, O, and S. The term "heteroaryl" may be used interchangeably with the terms "heteroaryl ring", "heteroaryl group", or "heteroaromatic". A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, and pyrazinyl. Bi-cyclic heteroaryls include groups in which a monocyclic heteroaryl ring is fused to one or more aryl or heteroaryl rings. Nonlimiting examples include indolyl, benzooxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrrolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached.

The term "heterocyclyl" means a 4- to 12-membered ring system, which is saturated or partially unsaturated (but not aromatic), containing 1 to 4 heteroatoms independently selected from N, O, and S. The terms "heterocycle", "heterocyclyl", "heterocyclyl ring", "heterocyclic group", and "heterocyclic moiety", are used interchangeably herein. A heterocyclyl ring can be attached to its pendant group at any heteroatom or carbon atom that results in a stable structure. A heterocyclyl group may be mono- or bicyclic. Examples of monocyclic saturated or partially unsaturated heterocyclic groups include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. Bi-cyclic heterocyclyl groups include, e.g., a heterocyclic ring fused to another unsaturated heterocyclic, cycloalkyl, aromatic or heteroaryl ring, such as for example, benzodioxolyl, dihydrobenzodioxinyl, 6,7-dihydro-5H-pyrrolo[2,1-c][1,2,4]triazolyl, 5,6,7,8-tetrahydroimidazo[1,2-a]pyridinyl, 1,2-dihydroquinolinyl, dihydrobenzofuranyl, tetrahydronaphthyridine, indolinone, dihydropyrrolotriazole, quinolinone, dioxaspirodecane. It will be understood that when specified, optional substituents on a heterocyclyl group may be present on any substitutable position and, include, e.g., the position at which the heterocyclyl is attached.

The term "cyclic moiety" refers to a saturated, unsaturated, or partially saturated monocyclic or polycyclic ring system. Such rings systems included, e.g., a carbocyclyl, aryl, heteroaryl, or heterocyclyl as defined above.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

The term "pharmaceutically acceptable salt" is a salt of a basic group (e.g., an amino group) or of an acidic group (e.g., a sulfonic acid) on the compounds described herein. Illustrative salts of a basic group include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, camphorsulfonate, and pamoate (i.e., 1,1'-methylene-bis-(2-hydroxy-3-naphthoate)) salts. Illustrative salts of an acidic group include, but are not limited, to lithium, sodium, potassium, calcium, magnesium, aluminum, chromium, iron, copper, zinc, cadmium, ammonium, guanidinium, pyridinium, and organic ammonium salts.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. In one aspect, pharmaceutically acceptable refers to a compound or composition that is approved or approvable by a regulatory agency of the Federal or state government or listed in the U.S. Pharmacopoeia or other generally recognized pharmacopoeia for use in animals and more particularly in humans.

The term "pharmaceutically acceptable carrier" refers to a non-toxic carrier, adjuvant, or vehicle that does not destroy the pharmacological activity of the compound with which it is formulated. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "subject" and "patient" are used interchangeably. In one aspect, the subject is a human. In some aspects, the subject is human age 85 years old or less. In other aspects, the subject is human age 65-85 years old. In yet other aspects, the subject is human age 58 years old or older.

3-sulfopropanoic acid and 3-SPA are used interchangeably and refer to the compound having the structure

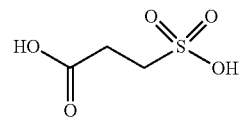

as well as the mono-

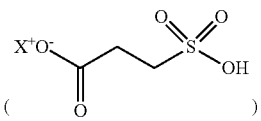

or di-ionic

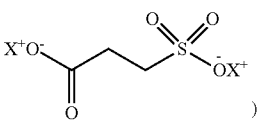

salt forms, where X⁺ is a counter ion such as sodium.

As used herein, the term "treat", "treating" or "treatment" means reversing, alleviating, or inhibiting the progress of a neurodegenerative disease such as AD, or one or more symptoms associated therewith.

Factors for determining if a subject is suffering from AD include e.g., one or more of the subject's MMSE score, the presence of brain amyloid (e.g., as determined by PET imaging), the subject's CDR score, FCSR memory test results consistent with mild cognitive impairment, or the identification of brain biomarkers of amyloid in the cerebrospinal fluid (CSF) such as Abeta-40, Abeta-42, tau protein, or Abeta oligomers, or combinations thereof. For example, a subject is suffering from AD if 1) the subject is homozygous for APOE4 and has cognitive symptoms; 2) the subject is homozygous for APOE4 and has subjective memory impairments, MCI, or an MMSE of 30, and the subject has an abnormal FCSR; 3) the subject the subject is homozygous for APOE4 and has early AD symptoms such as MCI or an MMSE of 26-30 and a CDR global score of 0.5; 4) the subject is heterozygous for APOE4 and has an MMSE of less than 20; 5) the subject is heterozygous for APOE4 and has an MMSE of 20 or greater, and the subject has brain amyloid as determined by one or more of the methods described herein (e.g., PET imaging or CSF biomarkers selected from Abeta-40, Abeta-42, and tau protein, or for Abeta oligomers); or 6) the subject is APOE4 negative and the subject has an MMSE score of 20 or higher or an MMSE score of less than 20 and the subject has brain amyloid as determined by one or more of the methods described herein (e.g., PET imaging or CSF biomarkers selected from Abeta-40, Abeta-42, and tau protein, or for Abeta oligomers). For classification of abnormal FCSR see e.g., E. Grober, R. B Lipton, C. Hall et al; Neurology 2000; 54: 827-832.

"Effective amount" or "effective dose" is the quantity of the compound which is sufficient to treat a neurodegenerative disease such as AD. Effective amounts can vary, as recognized by one of ordinary skill in the art, depending on e.g., the severity of the neurodegenerative disease, the route of administration, the sex, age and general health condition of the patient, excipient usage, the possibility of co-usage with other therapeutic treatments such as use of other agents and the judgment of the treating physician or other medical provider. Exemplary effective amounts of the compounds useful in the methods described herein are provided below. In some aspects, an effective amount is an amount that increases CSF 3-SPA concentration above the pre-determined baseline threshold. In more specific aspects, an effective amount is an amount that increases CSF 3-SPA concentration to 1.1×, 1.2×, 1.3×, 1.4×, 1.5×, 2×, 2.5×, 3×, 4×, 5×, or more than the pre-determined baseline threshold.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition. Exemplary regimens are provided below.

"Pre-determined baseline threshold", "pre-determined baseline level", or "certain baseline level" in the present methods (e.g., as in the first through tenth, twelfth, and fifteenth embodiment) are used interchangeably and refer to one or more of the following: (1) the 3-SPA CSF concentration (±10%) value determined for a MMSE of 30 in the line of best fit between the concentration of 3-SPA and MMSE scores in a random population of subjects with Alzheimer's Disease of varying degrees of severity (a "Random AD Population"); (2) the highest 3-SPA CSF concentration (±10%) determined in a Random AD Population for MMSE ≤29; (3) a subject's own 3-SPA CSF concentration (±5%) determined prior to exhibiting any symptoms of AD; (4) the average 3-SPA CSF concentration (±5%) determined in an age-matched normal (non-AD) population; (5) for embodiments where subjects are further selected by being within a range of MMSE scores, the higher of: (a) the 3-SPA CSF concentration (±10%) value determined for a MMSE of 30 in the line of best fit between the concentration of 3-SPA and MMSE scores in a Random AD Population; or (b) the highest 3-SPA CSF concentration (±10%) determined in a Random AD Population for MMSE scores equal to or above the lowest MMSE score in the selection range (e.g., if the selection requires a MMSE score between 22-28, then (b) is the highest 3-SPA CSF concentration (±10%) determined in a Random AD Population for MMSE scores equal to or above 22); (6) the 3-SPA CSF concentration (±10%) value for the subject's MMSE score as determined by the line of best fit between the concentration of 3-SPA and MMSE scores in a random population of subjects. If not otherwise indicated, the value for a pre-determined baseline threshold obtained using any of the parameters above, may be decreased or increased by up to 10% in order to be less or more inclusive of subjects to be treated, and to reduce the number of false positives or false negatives. The random population of subjects with Alzheimer's Disease is a randomly selected sampling of AD patients by degree of severity of their Alzheimer's Disease (e.g., by degree of cognitive decline or by their MMSE score), age, weight, general health, sex, diet, and the like, and can comprise e.g., at least 10, at least 15, at least 20, at least 25, at least 50, at least 75, at least 100, at least 500, at least 1000 subjects. In one aspect, however, the population of subjects has an average age of 85 years old or less. In other aspects, the population of subjects has an average age of 65-85 years old. In yet other aspects, the population of subjects has an average age of 58 years old or older. In some aspects, when the selection criteria additionally include ApoE4 status, the random population of subjects with Alzheimer's Disease of varying degrees of severity from which to derive the best fit line or determine the highest level of 3-SPA CSF concentration is limited to those AD subjects having the same ApoE4 status as the ApoE4 status selection criteria.

2. Uses/Methods

In a first embodiment, provided herein is method of treating a disease characterized by amyloid aggregates (e.g., Alzheimer's disease) in a subject in need thereof, comprising the step of administering to the subject an effective amount of a compound of Formula I:

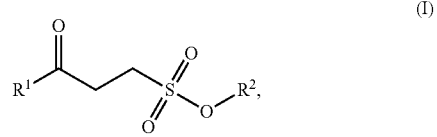

or a pharmaceutically acceptable salt thereof, wherein:
$R^1$ is selected from $-O-R^3$, $-O-R^4-CH(NHR^6)-C(O)-R^5$, and $-[N(R^6)-CH(R^7)-C(O)]_{1-2}-R^5$;
$R^2$ is selected from hydrogen, $R^3$, and $R^4-CH(NHR^6)-C(O)-O-R^5$;
each $R^3$ is independently selected from $C_1$-$C_{20}$ alkyl, $-C_2$-$C_{20}$ alkenyl, $-C_2$-$C_{20}$ alkynyl, $-(C_0$-$C_{20}$ alkylene)-aryl, $-(C_0$-$C_{20}$ alkylene)-carbocyclyl, $-(C_0$-$C_{20}$ alkylene)-heterocyclyl, $-(C_0$-$C_{20}$ alkylene)-heteroaryl, $-(C_2$-$C_{20}$ alkenylene)-aryl, $-(C_2$-$C_{20}$ alkenylene)-carbocyclyl, $-(C_2$-$C_{20}$ alkenylene)-heterocyclyl, $-(C_2$-$C_{20}$ alkenylene)-heteroaryl, $-(C_2$-$C_{20}$ alkynylene)-aryl, $-(C_2$-$C_{20}$ alkynylene)-carbocyclyl, $-(C_2$-$C_{20}$ alkynylene)-heterocyclyl, and $-(C_2$-$C_{20}$ alkynylene)-heteroaryl;
each $R^4$ is an independently selected derivatized side chain of a natural or unnatural α-amino acid wherein the side chain has been derivatized through a free $-OH$ group present on the side chain prior to derivatization;
each $R^5$ is independently selected from $-OH$, $-O-C_1$-$C_4$ alkyl and $-NH_2$;
each $R^6$ is independently selected from hydrogen and $-C(O)R^8$;
$R^7$ is a side chain of an α-amino acid; and
each $R^8$ is independently selected from hydrogen, $C_1$-$C_4$ alkyl, $-O-C_1$-$C_4$ alkyl, $-(C_1$-$C_4$ alkylene)-aryl, and $(C_1$-$C_4$ alkoxy)-aryl;
wherein:
each alkyl, alkylene, alkenyl, alkenylene, alkynyl or alkynylene portion of $R^3$ is optionally substituted with up to 6 substituents independently selected from halo, —OH, —O—($C_1$-$C_4$ alkyl), —O—($C_1$-$C_4$ haloalkyl), carbocyclyl, aryl, heterocyclyl, and heteroaryl;

each carbocyclyl, aryl, heterocyclyl, or heteroaryl portion of $R^3$ is optionally substituted with up to four substituents independently selected from halo, —OH, —O—($C_1$-$C_4$ alkyl), —O—($C_1$-$C_4$ haloalkyl), $C_1$-$C_{18}$ alkyl, $C_2$-$C_{18}$ alkenyl, and $C_2$-$C_{18}$ alkynyl, wherein the alkyl, alkenyl, or alkynyl portions of the $C_1$-$C_{18}$ alkyl, $C_2$-$C_{18}$ alkenyl, or $C_2$-$C_{18}$ alkynyl, respectively, are optionally substituted with up to six substituents independently selected from halo, —OH, —O—($C_1$-$C_4$ alkyl), and —O—($C_1$-$C_4$ haloalkyl);

$R^1$ comprises no more than 2 cyclic moieties; and $R^2$ comprises no more than 2 cyclic moieties.

Diseases characterized by amyloid aggregates include, but are not limited to, Alzheimer's disease including familial (hereditary) forms thereof, Down's syndrome dementia, Parkinson's Disease, Acute macular degeneration (AMD), glaucoma, Inclusion Body Myositis (IBM), traumatic brain injury, Lewy Bodies dementia, Huntington's disease, Nieman-Picks Type C, Cerebral Amyloid Angiopathy (CAA), Creutzfeldt-Jakob disease, AA Amyloidosis, AL Amyloidosis, ATTR amyloidosis, Familial amyloid polyneuropathy (FAP), Familial amyloid cardiomyopathy (FAC), Senile systemic amyloidosis, and prion disease. In one aspect, the disease characterized by amyloid aggregates is Alzheimer's disease.

In a second embodiment, provided is a method of selecting and treating a subject suffering from Alzheimer's disease comprising the steps of:

a) selecting the subject if the concentration of 3-SPA present in the subject is less than a pre-determined baseline threshold; and b) administering to selected subject an effective amount of a compound having the Formula I:

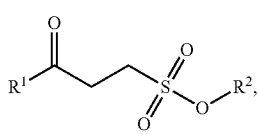

(I)

or a pharmaceutically acceptable salt thereof, wherein the variables for Formula I are as described above in the first embodiment.

In a third embodiment, provided herein is a method of treating a subject suffering from Alzheimer's disease comprising the steps of:

a) determining if 3-SPA is present in the subject at a concentration less than a pre-determined baseline threshold; and b) administering to the selected subject an effective amount of a compound having the Formula I:

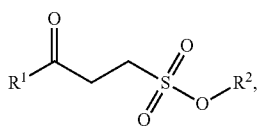

(I)

or a pharmaceutically acceptable salt thereof, wherein the variables for Formula I are as described above in the first embodiment.

Subjects in the present methods may be stratified (i.e., further selected) by their MMSE scores prior to treatment. In an fourth embodiment for example, the subject being treated in the embodiments described herein (e.g., as in the first, second, or third embodiment) has an MMSE score of greater than 19 (e.g., greater than 20, greater than 21, greater than 22, greater than 23, greater than 24, greater than 25, or greater than 26) prior to treatment. In another aspect, the subject being treated in the embodiments described herein (e.g., as in the first, second, or third embodiment) has an MMSE score of 16 to 30 (e.g., an MMSE score of 22 to 30, an MMSE score of 22 to 28, an MMSE score of 16 to 19, an MMSE score of 18 to 26, an MMSE score of 20 to 26, or an MMSE score of 22 to 26) prior to treatment.

In addition to the MMSE score, the subject may also have certain genetic factors such as the presence of APOE4 alleles (e.g., homo- or heterozygous for APOE4) or have other amyloid markers such as the presence of brain amyloid, or both. Subjects described herein may also have at least one ε4 allele of APOE. For example, in a fifth embodiment, the subject being treated in the embodiments described herein (e.g., as in the first, second, third, or fourth embodiment) is APOE4 heterozygous prior to treatment. Alternatively, in a sixth embodiment, the subject being treated in the embodiments described herein (e.g., as in the first, second, third, or fourth embodiment) is APOE4 homozygous prior to treatment. The term "heterozygous for APOE4" and "APOE4 heterozygous" are used interchangeably and refer to subjects having one APOE4 allele. The term "homozygous for APOE4", "APOE4 homozygous", "homozygous for APOE4/4", and "APOE4/4 homozygous" are used interchangeably and refer to subjects having two APOE4 alleles. In a more specific aspect of the sixth embodiment, the subject is selected for treatment if he or she is APOE4 homozygous and has a MMSE score of 22-28.

In a seventh embodiment, provided herein is a method of preventing Alzheimer's disease or cognitive decline in a subject (e.g., a subject who has AD or dementia due to head trauma) comprising the step of administering to the subject in need thereof a compound having the Formula I:

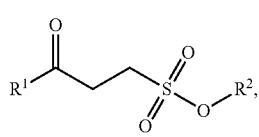

(I)

or a pharmaceutically acceptable salt thereof, wherein the variables for Formula I are as described above in the first embodiment.

In an eighth embodiment, the subject in the seventh embodiment is in need of prevention if one or more of the following are present: a) the level of 3-SPA in the subject is below a pre-determined baseline threshold; b) the subject has at least one ApoE4 allele; or c) the subject has a familial history of Alzheimer's disease. Alternatively, the subject in the seventh embodiment is in need of prevention if one or more of the following are present: a) the level of 3-SPA in the subject is below a pre-determined baseline threshold; b) the subject has at least two ApoE4 allele; or c) the subject has a familial history of Alzheimer's disease.

In a ninth embodiment, provided herein a method of preventing dementia in a subject (e.g., a subject who has AD or dementia due to head trauma) comprising the step of administering to the subject in need thereof a compound of the formula

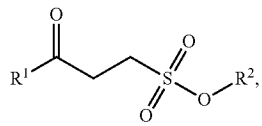

or a pharmaceutically acceptable salt thereof, wherein the variables for Formula I are as described above in the first embodiment.

In a tenth embodiment, the dementia in the ninth embodiment is related to a head injury (e.g., head trauma). Head injury occurs when an outside force hits the head hard enough to cause the brain to move violently within the skull. This force can cause shaking, twisting, bruising (contusion), or sudden change in the movement of the brain (concussion). It will be understood that even relatively mild head injuries can case prolonged or permanent declines in cognition.

In an eleventh embodiment, the dementia in the ninth embodiment is related to a head injury and the subject in the thirteenth embodiment is in need of prevention if the level of 3-SPA in the subject is below a pre-determined baseline threshold.

In one aspect, the concentration of 3-SPA present in the subject of the described methods (e.g., as in the second through fifth, eighth, and eleventh embodiment) is determined from a sample of cerebrospinal fluid. Thus, in one aspect, the pre-determined baseline threshold of 3-SPA in the subject is the baseline concentration of 3-SPA in the cerebral spinal fluid (CSF) of the subject obtained prior to exhibiting symptoms of AD and/or at a time when the subject's MMSE was 30.

In one aspect, the pre-determined baseline threshold of 3-SPA in the present methods (e.g., as in the first through tenth, twelfth, and fifteenth embodiment) is defined as an 3-SPA concentration in a subject of less than 25 ng/ml (e.g., less than 20 ng/ml, less than 15 ng/ml, less than 12 ng/ml, less than 10 ng/ml, less than 8 ng/ml, less than 6 ng/ml, less than 5 ng/ml, less than 4 ng/ml, less than 3 ng/ml, less than 2.9 ng/ml, less than 2.8 ng/ml, less than 2.7 ng/ml, less than 2.6 ng/ml, less than 2.5 ng/ml, less than 2.4 ng/ml, less than 2.3 ng/ml, less than 2.2 ng/ml, less than 2.1 ng/ml, less than 2.0 ng/ml). In other aspects, the pre-determined baseline threshold of 3-SPA is defined as a 3-SPA concentration in a subject of between 2.0 ng/ml and 25 ng/mL (e.g., between 7 ng/ml and 25 ng/mL, between 8 ng/ml and 25 ng/mL, between 9 ng/ml and 25 ng/mL, between 6 ng/ml and 24 ng/mL, or between 6 ng/ml and 23 ng/mL.

In one aspect, the pre-determined baseline threshold of 3-SPA in the present methods (e.g., as in the first through tenth, twelfth, and fifteenth embodiment) is defined as a subject having an MMSE score of 22-28 or an MMSE score of 22-26; and a 3-SPA concentration (e.g., in CSF) of less than 5 ng/mL, less than 4 ng/ml, less than 3 ng/ml, less than 2.9 ng/ml, less than 2.8 ng/ml, less than 2.7 ng/ml, less than 2.6 ng/ml, less than 2.5 ng/ml, less than 2.4 ng/ml, less than 2.3 ng/ml, less than 2.2 ng/ml, less than 2.1 ng/ml, less than 2.0 ng/ml. In other aspects, the pre-determined baseline threshold of 3-SPA in the present methods (e.g., as in the first through tenth, twelfth, and fifteenth embodiment) is defined as a subject having an MMSE score of 22-28 or an MMSE score of 22-26 and a 3-SPA concentration (e.g., in CSF) of 2-4 ng/mL.

In a twelfth embodiment, provided herein is a method for treating a subject suffering from AD, comprising administering to the subject an effective amount of a compound having the Formula I as defined herein, or a pharmaceutically acceptable salt thereof, wherein the subject has MMSE score of 30, is homozygous for APOE4, and has an abnormal FCSR memory test indicating MCI. For classification of abnormal FCSR see e.g., E. Grober, R. B Lipton, C. Hall et al; Neurology 2000; 54: 827-832.

In a thirteenth embodiment, provided herein a method for selecting and treating a subject suffering from AD, comprising: a) selecting a subject having a MMSE score of 22-28; and b) administering to the selected subject an effective amount of a compound having the Formula I as defined herein, or a pharmaceutically acceptable salt thereof.

In a fourteenth embodiment, provided herein is a method for selecting and treating a subject suffering from AD, comprising: a) selecting a subject who is APOE4 homozygous or APOE4 heterozygous; and b) administering to the selected subject an effective amount of a compound having the Formula I as defined herein, or a pharmaceutically acceptable salt thereof.

In a fifteenth embodiment, provided herein is a method for selecting and treating a subject suffering from AD, comprising: a) selecting a subject having a MMSE score of 22-28 and is APOE4 homozygous or APOE4 heterozygous; and b) administering to the selected subject an effective amount of a compound having the Formula I as defined herein, or a pharmaceutically acceptable salt thereof.

In some aspects of the thirteenth through fifteenth embodiment, the subject is selected if the subject has a MMSE score of 22-26. In some aspects of the thirteenth through fifteenth embodiment, the subject is selected if the subject is APOE4 homozygous. In some aspects of the thirteenth through fifteenth embodiment, the subject is selected if the subject is APOE4 homozygous and has a MMSE score of 22-28. In some aspects of the thirteenth through fifteenth embodiment, the subject is selected if the subject is APOE4 homozygous and has a MMSE score of 22-26.

In a sixteenth embodiment, provided herein is a method for selecting and treating a subject suffering from AD, comprising: a) selecting a subject having an MMSE score of greater than 19 (e.g., greater than 20, greater than 21, greater than 22, greater than 23, greater than 24, greater than 25, or greater than 26) prior to treatment; and administering to the selected subject an effective amount of a compound having the Formula I as defined herein, or a pharmaceutically acceptable salt thereof. In another aspect, provided herein is a method for selecting and treating a subject suffering from AD, comprising: a) selecting a subject having an MMSE score of 16 to 30 (e.g., an MMSE score of 22 to 30, an MMSE score of 22 to 28, an MMSE score of 16 to 19, an MMSE score of 18 to 26, an MMSE score of 20 to 26, or an MMSE score of 22 to 26) prior to treatment; and administering to the selected subject an effective amount of a compound having the Formula I as defined herein, or a pharmaceutically acceptable salt thereof.

In a seventeenth embodiment, provided herein is a method for preventing AD comprising administering to a subject in need thereof an effective amount of a compound having the Formula I as defined herein, or a pharmaceutically acceptable salt thereof.

In an eighteenth embodiment, provided herein is a method for preventing a decline in cognition in a subject who is asymptomatic, but who is at risk for AD or cognitive decline comprising administering to a subject in need thereof an effective amount of a compound having the Formula I as defined herein, or a pharmaceutically acceptable salt thereof. Subjects who are at risk would include e.g., the presence of APOE4/4 (or both APOE4 and APOE4/4), advanced age, or a pattern of familial cognitive decline, or with a combination of two or more of the above.

In terms of preventing AD or preventing a decline in cognition in a subject who is asymptomatic, but who is at risk for AD or cognitive decline, we hypothesize from the data shown below that 3-SPA is always active in the brain preventing or inhibiting the formation of the toxic oligomers. Therefore, the lower the amount of 3-SPA, the greater the susceptibility a subject would have to developing cognitive decline, or to develop it earlier. Administration of compounds such as those described herein should produce more 3-SPA in the brain. This in turn should establish consistent and/or enhanced inhibition of Aβ oligomers and thereby lead to prevention of AD or a decline in cognition.

3. Compounds of the Present Uses/Methods

The compounds utilized in the present methods include those having the Formula I as defined above, or a pharmaceutically acceptable salt thereof.

Alternatively, in a sixteenth embodiment, the compounds utilized in the present methods include those having the Formula I as defined above, wherein $R^2$ is selected from hydrogen and $C_1$-$C_6$ alkyl, and wherein the remaining variables for the compound are as described above for Formula I. Alternatively, the compounds utilized in the present methods include those having the Formula I as defined above, wherein $R^2$ is —$CH_3$, and wherein the remaining variables are as described above for Formula I.

Alternatively, in a seventeenth embodiment, the compounds utilized in the present methods include those having the Formula I as defined above, wherein $12^1$ is selected from —O—$R^3$, —O—$R^4$—CH($NHR^6$)—C(O)—$R^5$, and —O—$R^4$—CH($NHR^6$)—CH(OH)—$R^5$; $R^3$ is $C_1$-$C_4$ alkyl; and $R^4$ is selected from —CH($CH_3$)—, —$CH_2$—,

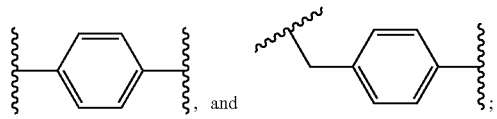

and wherein the remaining variables for the compound are as described above for Formula I, or the second embodiment.

Alternatively, in an eighteenth embodiment, the compounds utilized in the present methods include those having the Formula I as defined above, wherein $R^6$ is selected from hydrogen, —C(O)H, —C(O)$CH_3$, —C(O)O—C($CH_3$)$_3$, and —C(O)O-benzyl, and wherein the remaining variables for the compound are as described above for Formula I, or the second or third embodiment.

Alternatively, in a nineteenth embodiment, the compounds utilized in the present methods include those having the Formula I as defined above, wherein $R^5$ is selected from —OH, —$OCH_3$, and —$OCH_2CH_3$, and wherein the remaining variables for the compound are as described above for Formula I, or the second, third, or fourth embodiment.

Alternatively, in a twentieth embodiment, the compound of Formula I is selected from any compound in Table 1 or a pharmaceutically acceptable salt thereof:

TABLE 1

| # | Structure |
|---|---|
| 100 | 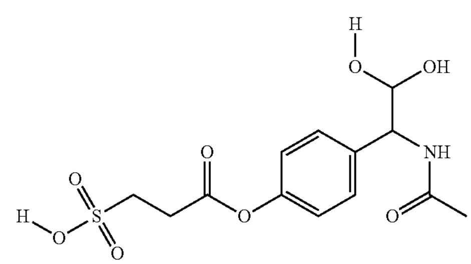 [SMILES: CC(=O)NC(c1ccc(OC(=O)CCS(=O)(=O)O)cc1)C(O)O] |
| 101 | 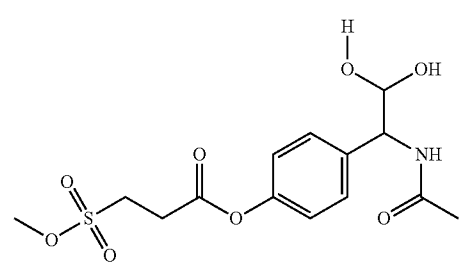 [SMILES: COS(=O)(=O)CCC(=O)Oc1ccc(C(NC(C)=O)C(O)O)cc1] |

TABLE 1-continued
| # | Structure |
|---|---|
| 102 | 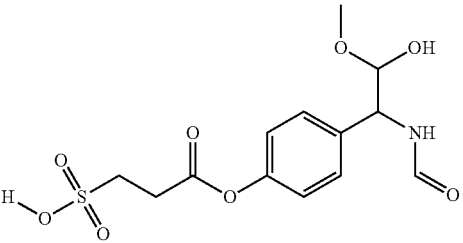 [SMILES: COC(O)C(NC=O)c1ccc(OC(=O)CCS(=O)(=O)O)cc1] |
| 103 | 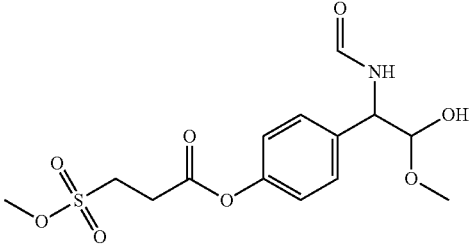 [SMILES: COC(O)C(NC=O)c1ccc(OC(=O)CCS(=O)(=O)OC)cc1] |
| 104 | 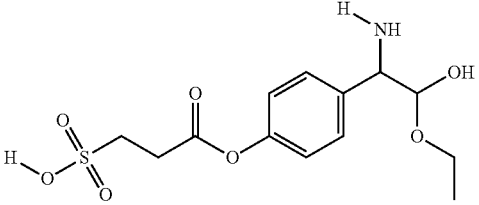 [SMILES: CCOC(O)C(N)c1ccc(OC(=O)CCS(=O)(=O)O)cc1] |
| 105 | 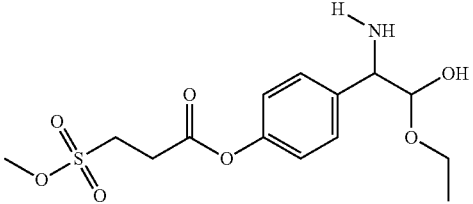 [SMILES: CCOC(O)C(N)c1ccc(OC(=O)CCS(=O)(=O)OC)cc1] |
| 106 | 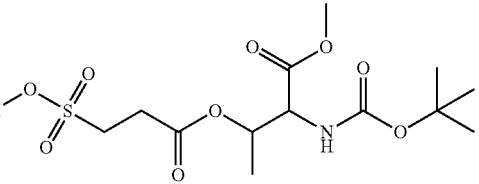 |
| 107 | 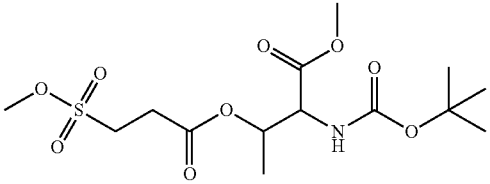 [SMILES: COC(=O)C(NC(=O)OC(C)(C)C)C(C)OC(=O)CCS(=O)(=O)OC] |
| 108 | 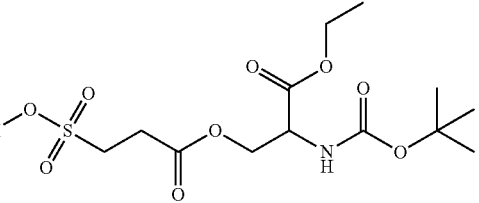 |

TABLE 1-continued

| # | Structure |
|---|-----------|
| 109 | 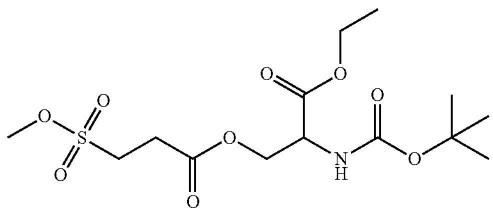 [SMILES: CCOC(=O)C(COC(=O)CCS(=O)(=O)OC)NC(=O)OC(C)(C)C] |
| 110 | 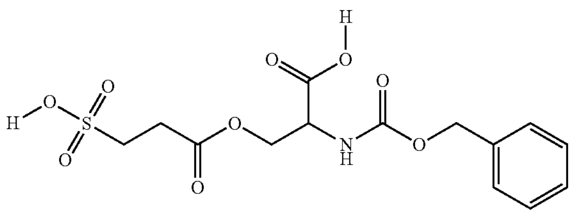 [SMILES: O=C(CCS(=O)(=O)O)OCC(NC(=O)OCc1ccccc1)C(=O)O] |
| 111 | 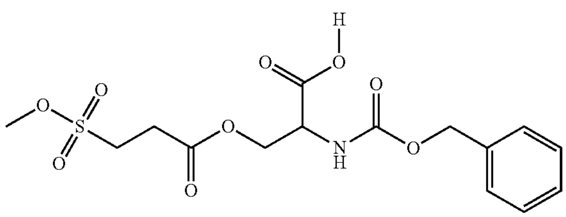 [SMILES: COS(=O)(=O)CCC(=O)OCC(NC(=O)OCc1ccccc1)C(=O)O] |
| 112 | 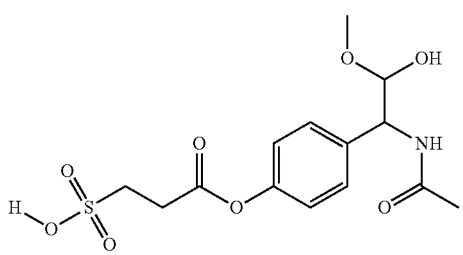 [SMILES: COC(O)C(NC(C)=O)c1ccc(OC(=O)CCS(=O)(=O)O)cc1] |
| 113 | 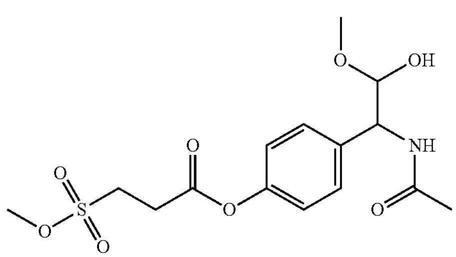 [SMILES: COC(O)C(NC(C)=O)c1ccc(OC(=O)CCS(=O)(=O)OC)cc1] |
| 114 | 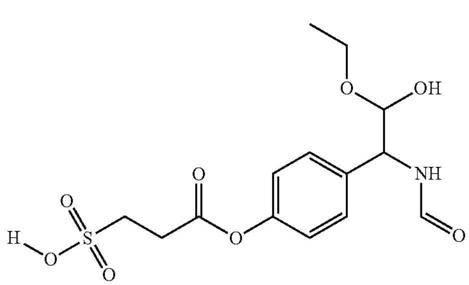 [SMILES: CCOC(O)C(NC=O)c1ccc(OC(=O)CCS(=O)(=O)O)cc1] |

TABLE 1-continued

| # | Structure |
|---|---|
| 115 | 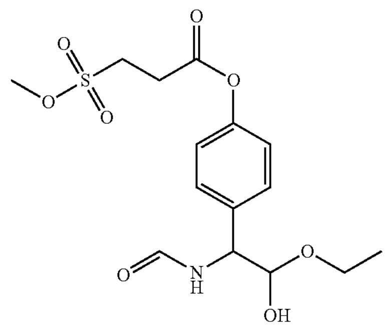 [SMILES: CCOC(O)C(NC=O)c1ccc(OC(=O)CCS(=O)(=O)OC)cc1] |
| 116 | 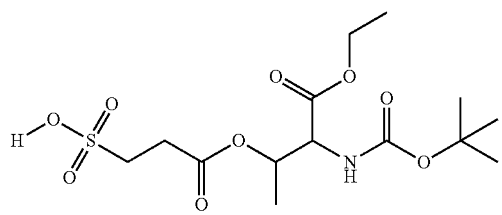 [SMILES: CCOC(=O)C(NC(=O)OC(C)(C)C)C(C)OC(=O)CCS(=O)(=O)O] |
| 117 | 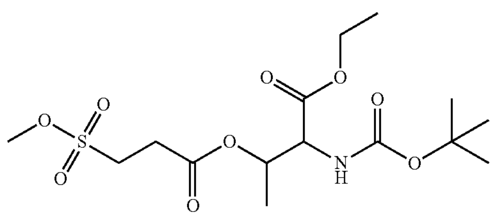 [SMILES: CCOC(=O)C(NC(=O)OC(C)(C)C)C(C)OC(=O)CCS(=O)(=O)OC] |
| 118 | 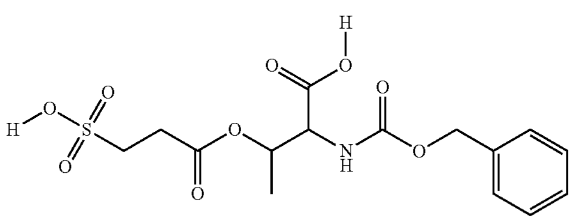 [SMILES: CC(OC(=O)CCS(=O)(=O)O)C(NC(=O)OCc1ccccc1)C(=O)O] |
| 119 | 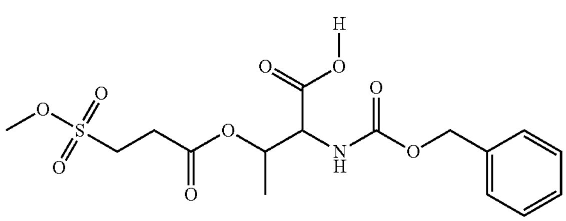 [SMILES: COS(=O)(=O)CCC(=O)OC(C)C(NC(=O)OCc1ccccc1)C(=O)O] |
| 120 | 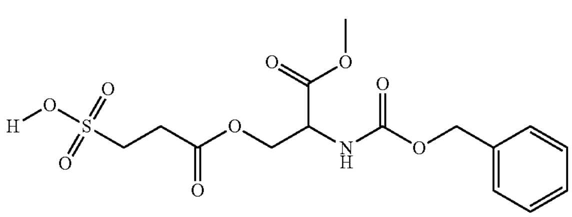 [SMILES: COC(=O)C(COC(=O)CCS(=O)(=O)O)NC(=O)OCc1ccccc1] |

TABLE 1-continued

| # | Structure |
|---|---|
| 121 | 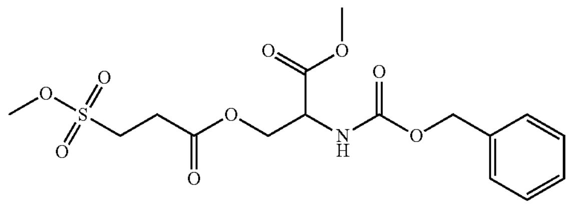 [SMILES: COC(=O)C(COC(=O)CCS(=O)(=O)OC)NC(=O)OCc1ccccc1] |
| 122 | 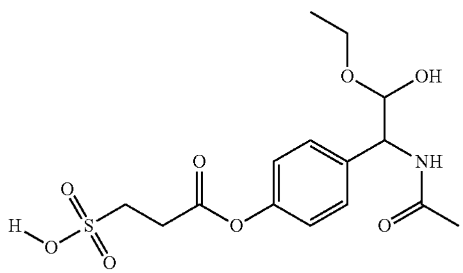 [SMILES: CCOC(O)C(NC(C)=O)c1ccc(OC(=O)CCS(=O)(=O)O)cc1] |
| 123 | 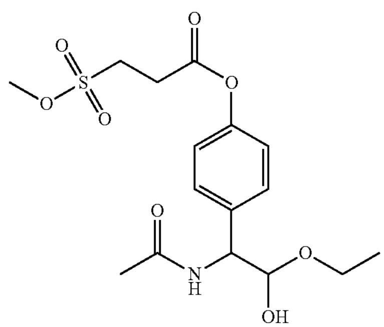 [SMILES: CCOC(O)C(NC(C)=O)c1ccc(OC(=O)CCS(=O)(=O)OC)cc1] |
| 124 | 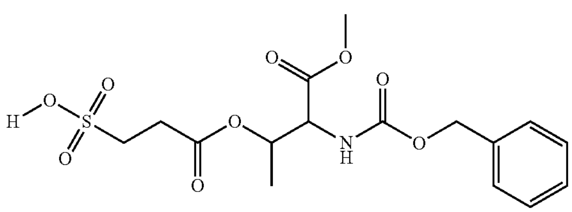 [SMILES: COC(=O)C(NC(=O)OCc1ccccc1)C(C)OC(=O)CCS(=O)(=O)O] |
| 125 | 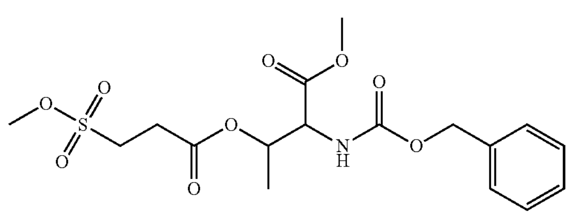 [SMILES: COC(=O)C(NC(=O)OCc1ccccc1)C(C)OC(=O)CCS(=O)(=O)OC] |
| 126 | 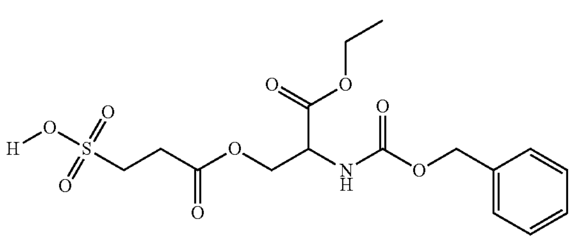 [SMILES: CCOC(=O)C(COC(=O)CCS(=O)(=O)O)NC(=O)OCc1ccccc1] |

TABLE 1-continued

| # | Structure |
|---|---|
| 127 | 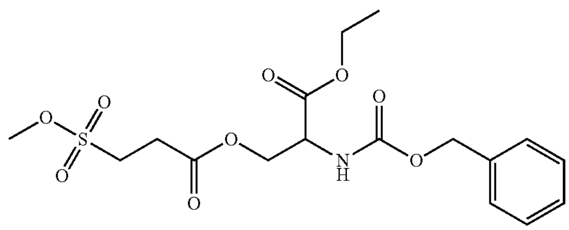 [SMILES: CCOC(=O)C(COC(=O)CCS(=O)(=O)OC)NC(=O)OCc1ccccc1] |
| 128 | 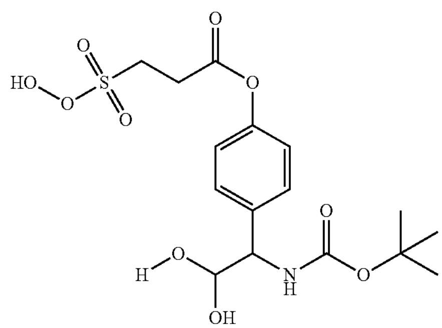 [SMILES: CC(C)(C)OC(=O)NC(c1ccc(OC(=O)CCS(=O)(=O)OO)cc1)C(O)O] |
| 129 | 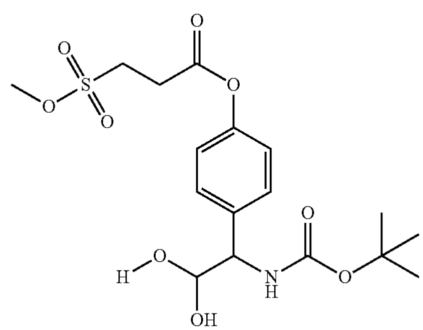 |
| 130 | 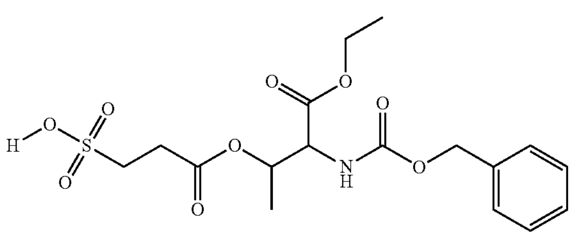 [SMILES: CCOC(=O)C(NC(=O)OCc1ccccc1)C(C)OC(=O)CCS(=O)(=O)O] |
| 131 | 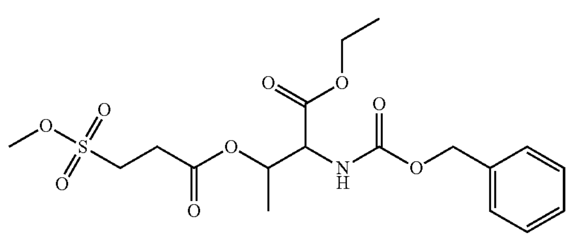 [SMILES: CCOC(=O)C(NC(=O)OCc1ccccc1)C(C)OC(=O)CCS(=O)(=O)OC] |

TABLE 1-continued

| # | Structure |
|---|---|
| 132 | 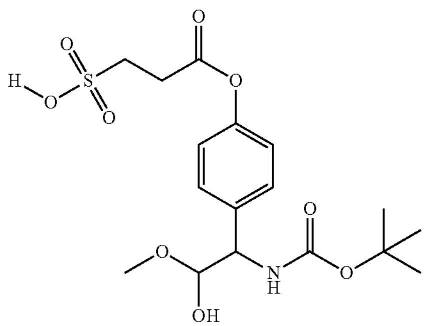 [SMILES: COC(O)C(NC(=O)OC(C)(C)C)c1ccc(OC(=O)CCS(=O)(=O)O)cc1] |
| 133 | 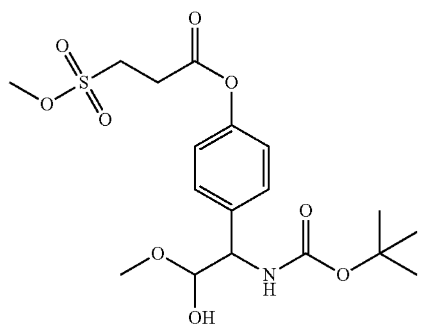 [SMILES: COC(O)C(NC(=O)OC(C)(C)C)c1ccc(OC(=O)CCS(=O)(=O)OC)cc1] |
| 134 | 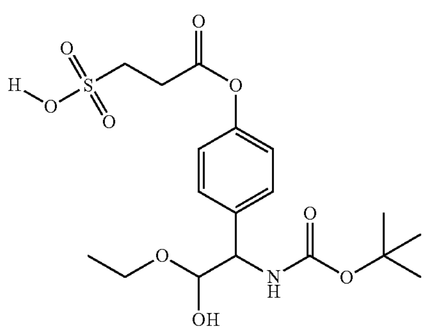 [SMILES: CCOC(O)C(NC(=O)OC(C)(C)C)c1ccc(OC(=O)CCS(=O)(=O)O)cc1] |
| 135 | 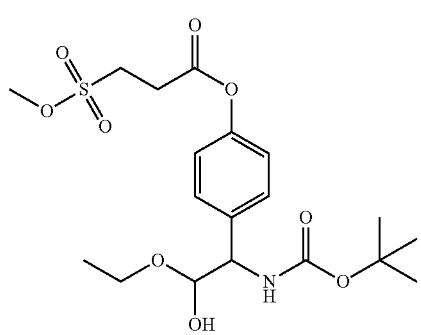 [SMILES: CCOC(O)C(NC(=O)OC(C)(C)C)c1ccc(OC(=O)CCS(=O)(=O)OC)cc1] |

TABLE 1-continued

| # | Structure |
|---|---|
| 136 | 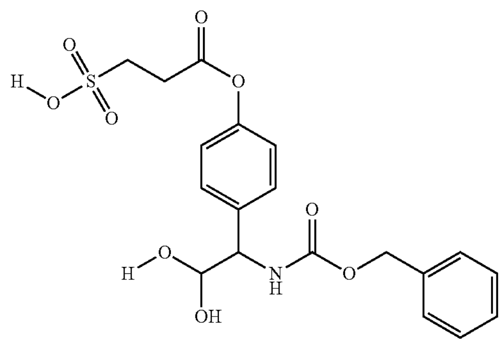 [SMILES: O=C(CCS(=O)(=O)O)Oc1ccc(C(NC(=O)OCc2ccccc2)C(O)O)cc1] |
| 137 | 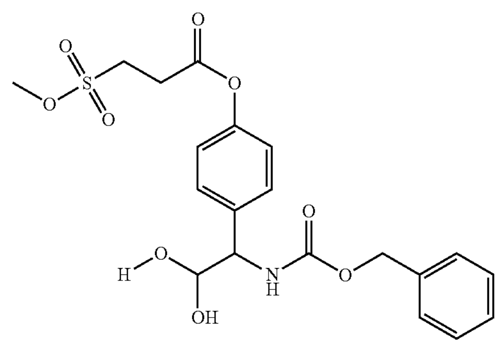 [SMILES: COS(=O)(=O)CCC(=O)Oc1ccc(C(NC(=O)OCc2ccccc2)C(O)O)cc1] |
| 138 | 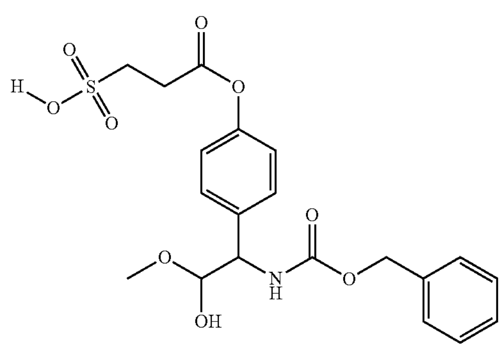 [SMILES: COC(O)C(NC(=O)OCc1ccccc1)c1ccc(OC(=O)CCS(=O)(=O)O)cc1] |
| 139 | 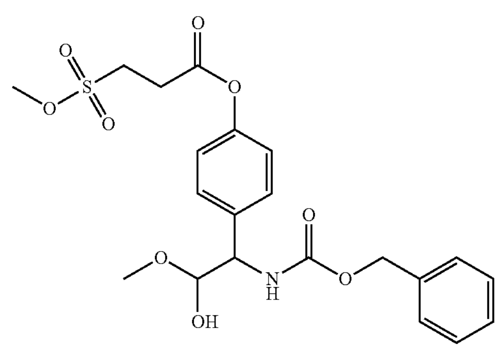 [SMILES: COC(O)C(NC(=O)OCc1ccccc1)c1ccc(OC(=O)CCS(=O)(=O)OC)cc1] |

TABLE 1-continued
| # | Structure |
|---|---|
| 140 | 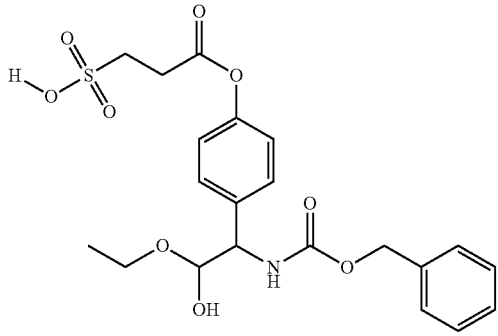 [SMILES: CCOC(O)C(NC(=O)OCc1ccccc1)c1ccc(OC(=O)CCS(=O)(=O)O)cc1] |
| 141 | 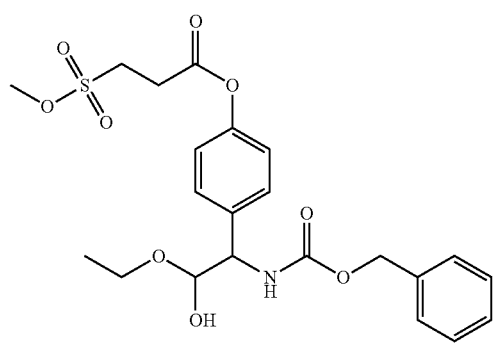 [SMILES: CCOC(O)C(NC(=O)OCc1ccccc1)c1ccc(OC(=O)CCS(=O)(=O)OC)cc1] |
| 142 | 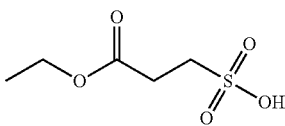 |
| 143 | 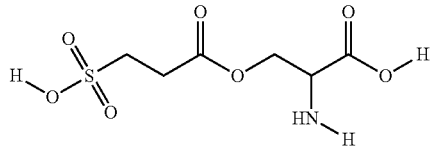 [SMILES: NC(COC(=O)CCS(=O)(=O)O)C(=O)O] |
| 144 | 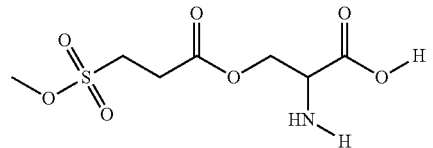 [SMILES: COS(=O)(=O)CCC(=O)OCC(N)C(=O)O] |
| 145 | 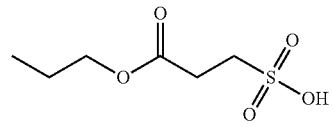 |
| 146 | 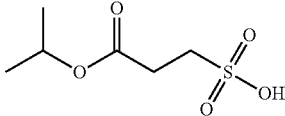 |

TABLE 1-continued
| # | Structure |
|---|---|
| 147 | 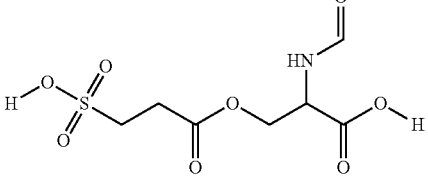 |
| 148 | 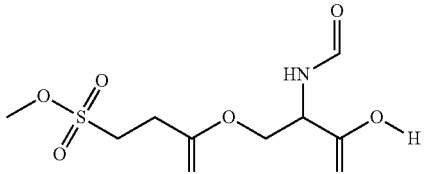 |
| 149 | 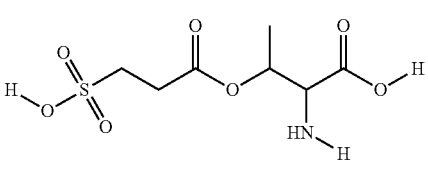 [SMILES: CC(OC(=O)CCS(=O)(=O)O)C(N)C(=O)O] |
| 150 | 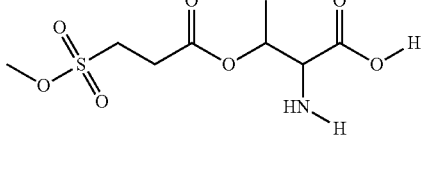 |
| 151 | 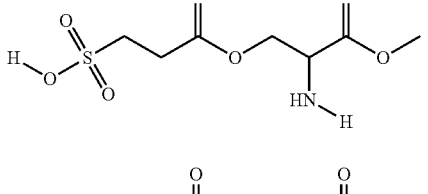 |
| 152 | 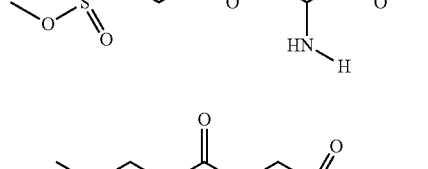 |
| 153 | 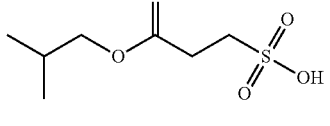 |
| 154 | 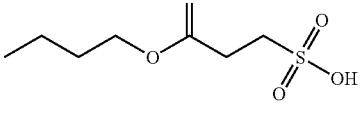 |
| 155 | 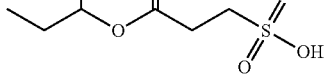 |

TABLE 1-continued

| # | Structure |
|---|---|
| 156 | 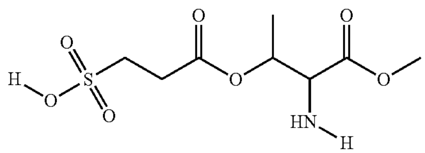 [SMILES: COC(=O)C(N)C(C)OC(=O)CCS(=O)(=O)O] |
| 157 | 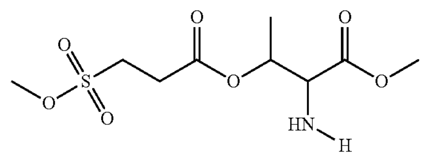 |
| 158 | 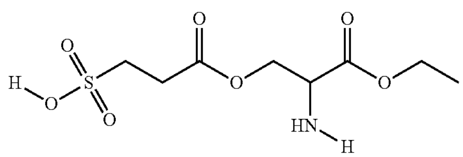 [SMILES: CCOC(=O)C(N)COC(=O)CCS(=O)(=O)O] |
| 159 | 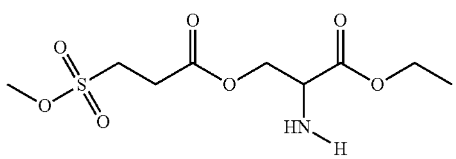 [SMILES: CCOC(=O)C(N)COC(=O)CCS(=O)(=O)OC] |
| 160 | 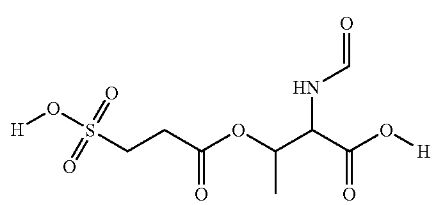 [SMILES: CC(OC(=O)CCS(=O)(=O)O)C(NC=O)C(=O)O] |
| 161 | 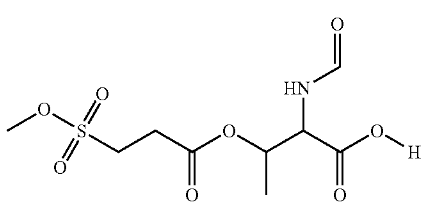 [SMILES: COS(=O)(=O)CCC(=O)OC(C)C(NC=O)C(=O)O] |
| 162 | 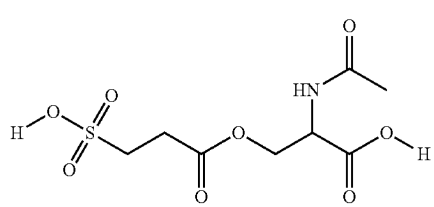 [SMILES: CC(=O)NC(COC(=O)CCS(=O)(=O)O)C(=O)O] |
| 163 | 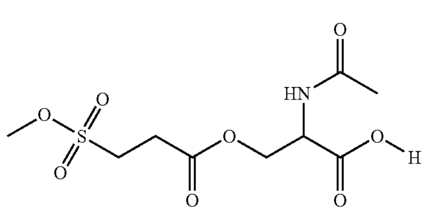 [SMILES: COS(=O)(=O)CCC(=O)OCC(NC(C)=O)C(=O)O] |

TABLE 1-continued

| # | Structure |
|---|---|
| 164 | 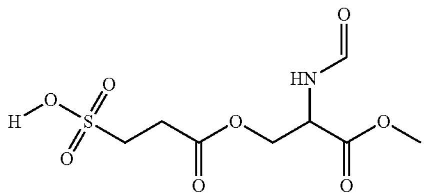 [SMILES: COC(=O)C(COC(=O)CCS(=O)(=O)O)NC=O] |
| 165 | 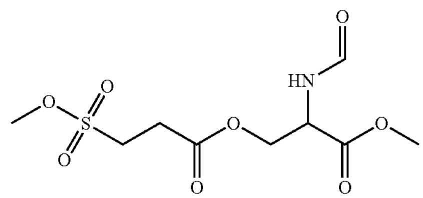 |
| 166 | 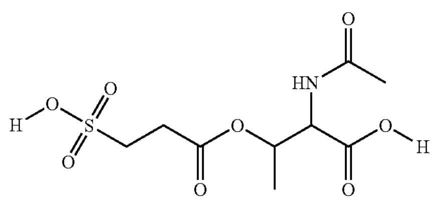 [SMILES: CC(=O)NC(C(=O)O)C(C)OC(=O)CCS(=O)(=O)O] |
| 167 | 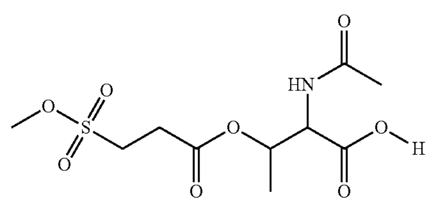 [SMILES: COS(=O)(=O)CCC(=O)OC(C)C(NC(C)=O)C(=O)O] |
| 168 | 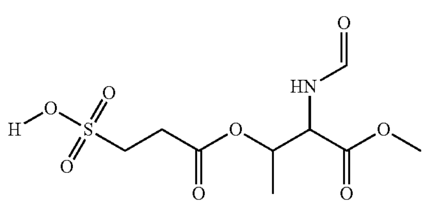 [SMILES: COC(=O)C(NC=O)C(C)OC(=O)CCS(=O)(=O)O] |
| 169 | 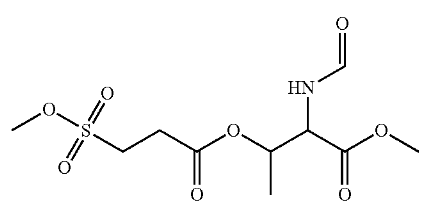 |
| 170 | 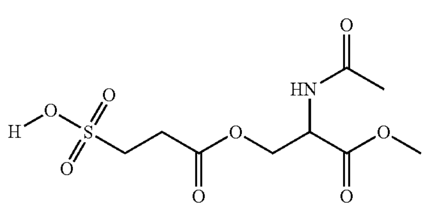 [SMILES: COC(=O)C(COC(=O)CCS(=O)(=O)O)NC(C)=O] |

TABLE 1-continued

| # | Structure |
|---|---|
| 171 | 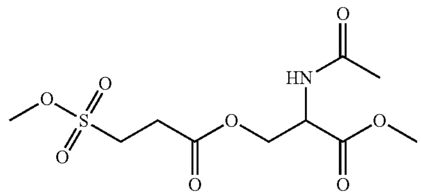 |
| 172 | 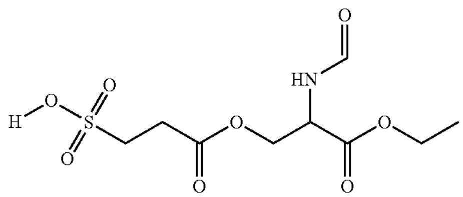 [SMILES: CCOC(=O)C(COC(=O)CCS(=O)(=O)O)NC=O] |
| 173 | 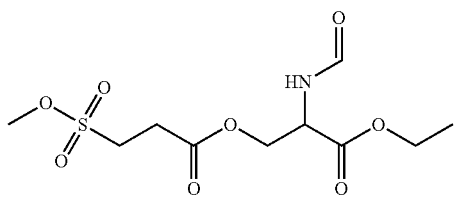 [SMILES: CCOC(=O)C(COC(=O)CCS(=O)(=O)OC)NC=O] |
| 174 | 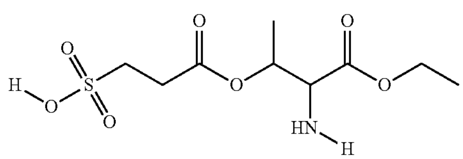 [SMILES: CCOC(=O)C(N)C(C)OC(=O)CCS(=O)(=O)O] |
| 175 | 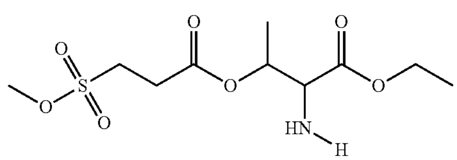 [SMILES: CCOC(=O)C(N)C(C)OC(=O)CCS(=O)(=O)OC] |
| 176 | 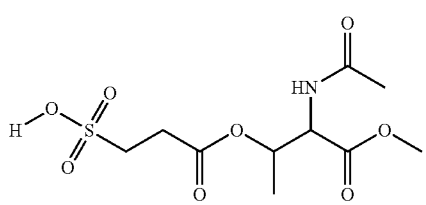 [SMILES: COC(=O)C(NC(C)=O)C(C)OC(=O)CCS(=O)(=O)O] |
| 177 | 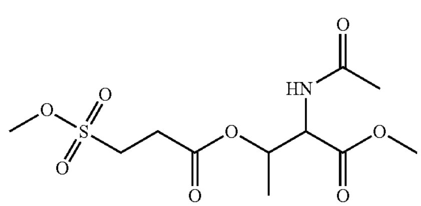 |
| 178 | 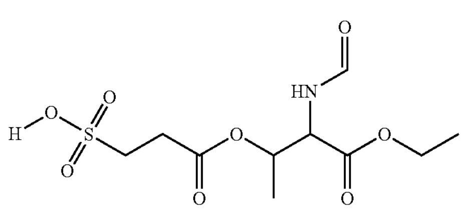 [SMILES: CCOC(=O)C(NC=O)C(C)OC(=O)CCS(=O)(=O)O] |

TABLE 1-continued

| # | Structure |
|---|---|
| 179 | 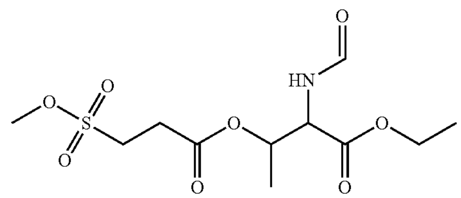 [SMILES: CCOC(=O)C(NC=O)C(C)OC(=O)CCS(=O)(=O)OC] |
| 180 | 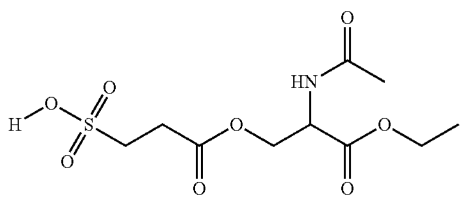 [SMILES: CCOC(=O)C(COC(=O)CCS(=O)(=O)O)NC(C)=O] |
| 181 | 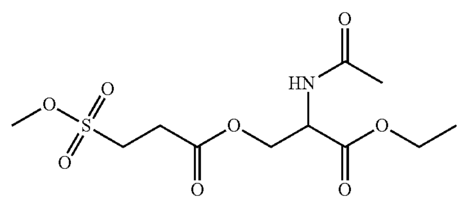 [SMILES: CCOC(=O)C(COC(=O)CCS(=O)(=O)OC)NC(C)=O] |
| 182 | 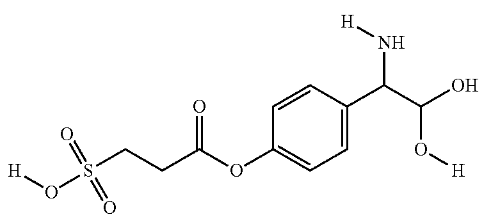 [SMILES: NC(c1ccc(OC(=O)CCS(=O)(=O)O)cc1)C(O)O] |
| 183 | 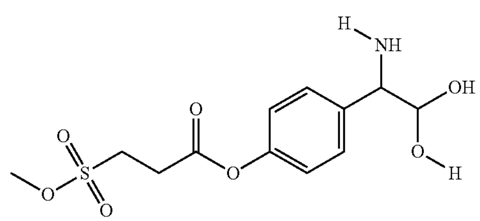 [SMILES: COS(=O)(=O)CCC(=O)Oc1ccc(C(N)C(O)O)cc1] |
| 184 | 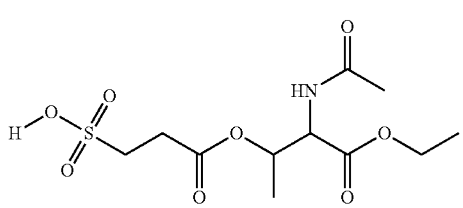 [SMILES: CCOC(=O)C(NC(C)=O)C(C)OC(=O)CCS(=O)(=O)O] |
| 185 | 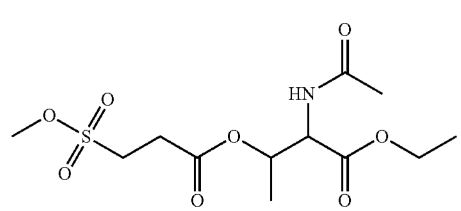 [SMILES: CCOC(=O)C(NC(C)=O)C(C)OC(=O)CCS(=O)(=O)OC] |

TABLE 1-continued
| # | Structure |
|---|---|
| 186 | 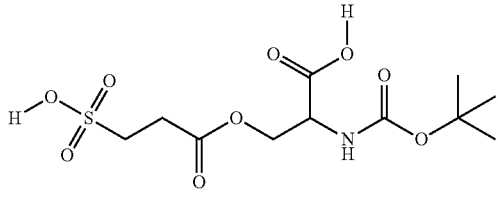 [SMILES: CC(C)(C)OC(=O)NC(COC(=O)CCS(=O)(=O)O)C(=O)O] |
| 187 | 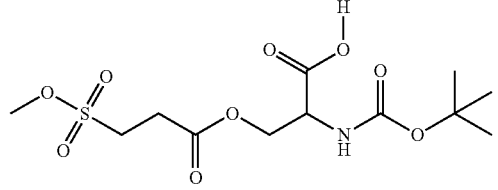 [SMILES: COS(=O)(=O)CCC(=O)OCC(NC(=O)OC(C)(C)C)C(=O)O] |
| 188 | 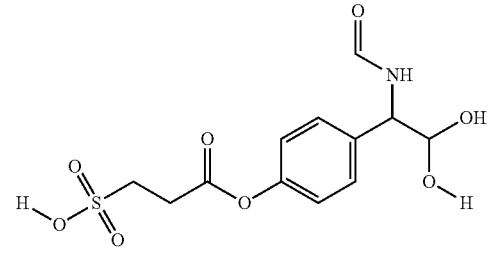 [SMILES: O=CNC(c1ccc(OC(=O)CCS(=O)(=O)O)cc1)C(O)O] |
| 189 | 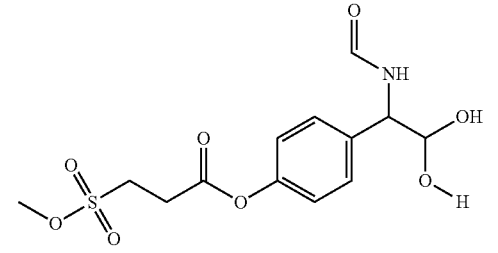 [SMILES: COS(=O)(=O)CCC(=O)Oc1ccc(C(NC=O)C(O)O)cc1] |
| 190 | 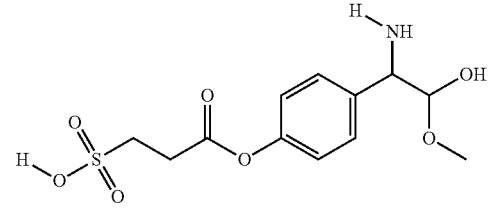 [SMILES: COC(O)C(N)c1ccc(OC(=O)CCS(=O)(=O)O)cc1] |
| 191 | 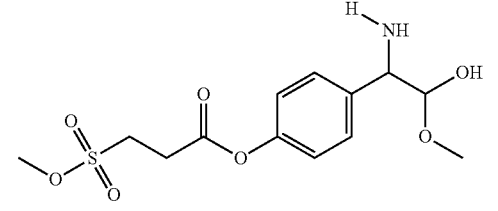 |
| 192 | 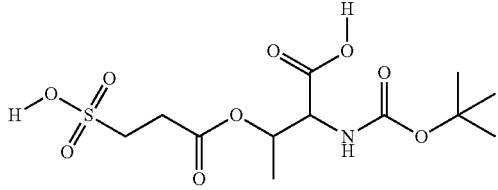 [SMILES: CC(OC(=O)CCS(=O)(=O)O)C(NC(=O)OC(C)(C)C)C(=O)O] |

TABLE 1-continued

| # | Structure |
|---|---|
| 193 | 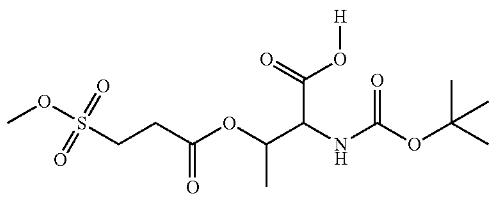 [SMILES: COS(=O)(=O)CCC(=O)OC(C)C(NC(=O)OC(C)(C)C)C(=O)O] |
| 194 | 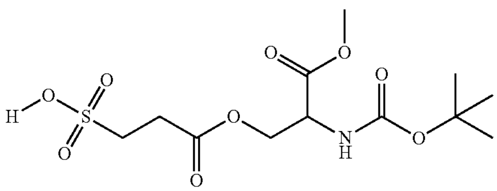 [SMILES: COC(=O)C(COC(=O)CCS(=O)(=O)O)NC(=O)OC(C)(C)C] |
| 195 | 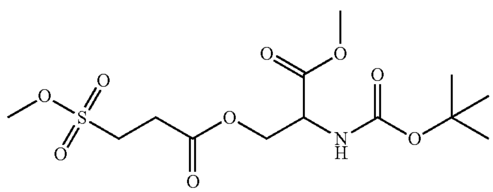 [SMILES: COC(=O)C(COC(=O)CCS(=O)(=O)OC)NC(=O)OC(C)(C)C] |
| 196 | 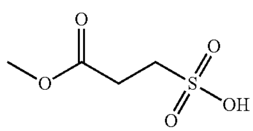 |
| 197 | 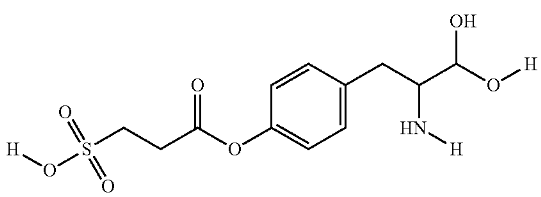 [SMILES: NC(Cc1ccc(OC(=O)CCS(=O)(=O)O)cc1)C(O)O] |
| 198 | 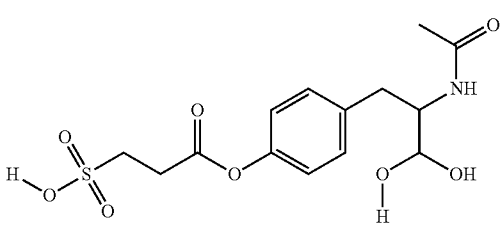 [SMILES: CC(=O)NC(Cc1ccc(OC(=O)CCS(=O)(=O)O)cc1)C(O)O] |
| 199 | 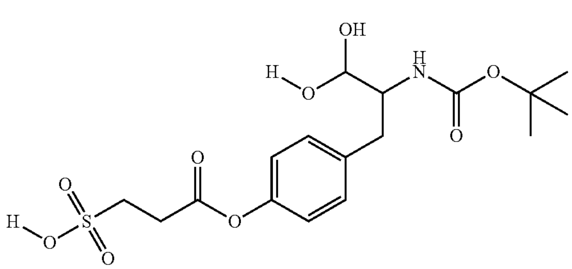 [SMILES: CC(C)(C)OC(=O)NC(Cc1ccc(OC(=O)CCS(=O)(=O)O)cc1)C(O)O] |

TABLE 1-continued
| # | Structure |
|---|---|
| 200 | 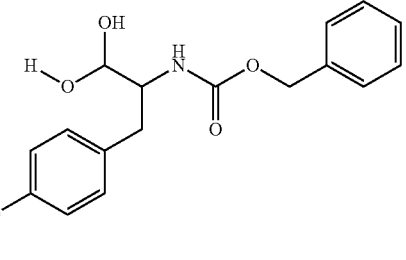 |
| 201 | 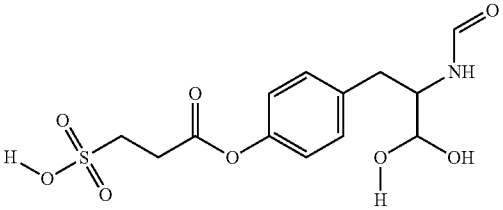 [SMILES: O=CNC(Cc1ccc(OC(=O)CCS(=O)(=O)O)cc1)C(O)O] |
| 202 | 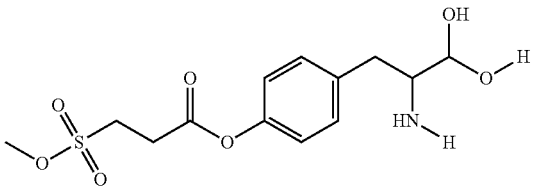 [SMILES: COS(=O)(=O)CCC(=O)Oc1ccc(CC(N)C(O)O)cc1] |
| 203 | 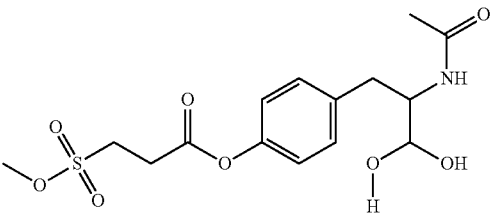 [SMILES: COS(=O)(=O)CCC(=O)Oc1ccc(CC(NC(C)=O)C(O)O)cc1] |
| 204 | 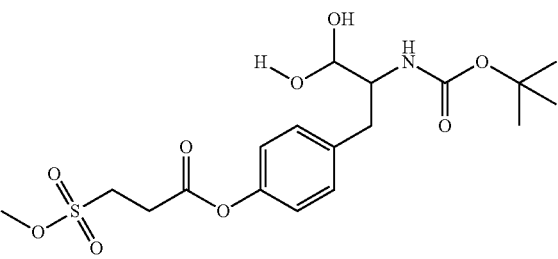 [SMILES: COS(=O)(=O)CCC(=O)Oc1ccc(CC(NC(=O)OC(C)(C)C)C(O)O)cc1] |
| 205 | 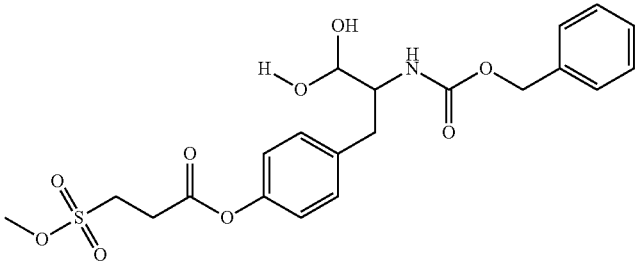 [SMILES: COS(=O)(=O)CCC(=O)Oc1ccc(CC(NC(=O)OCc2ccccc2)C(O)O)cc1] |

TABLE 1-continued

| # | Structure |
|---|---|
| 206 | 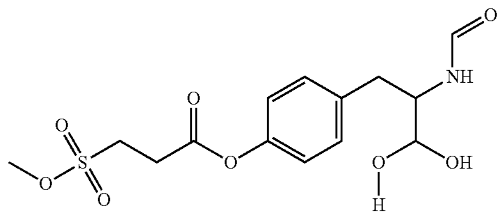 [SMILES: COS(=O)(=O)CCC(=O)Oc1ccc(CC(NC=O)C(O)O)cc1] |
| 207 | 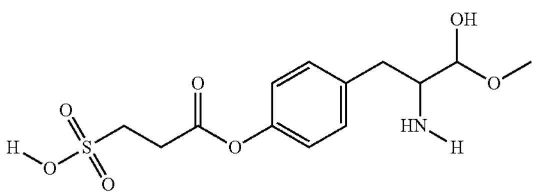 [SMILES: COC(O)C(N)Cc1ccc(OC(=O)CCS(=O)(=O)O)cc1] |
| 208 | 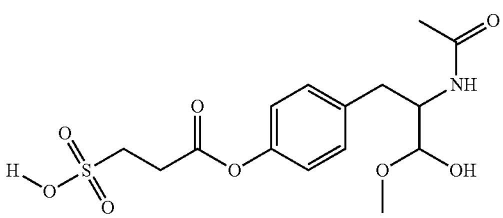 [SMILES: COC(O)C(Cc1ccc(OC(=O)CCS(=O)(=O)O)cc1)NC(C)=O] |
| 209 | 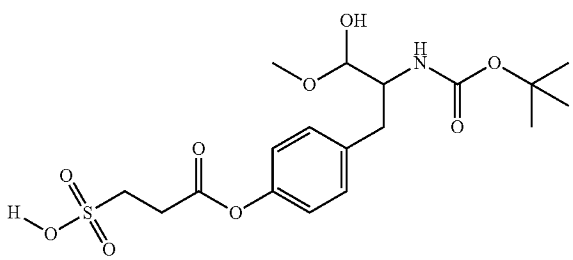 [SMILES: COC(O)C(Cc1ccc(OC(=O)CCS(=O)(=O)O)cc1)NC(=O)OC(C)(C)C] |
| 210 | 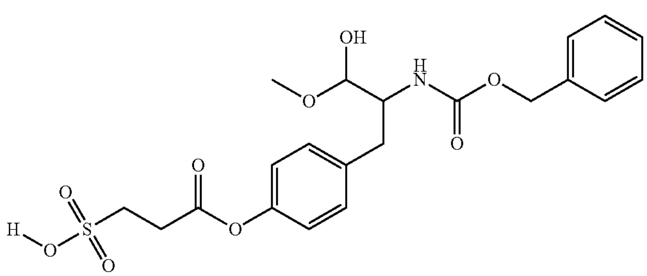 [SMILES: COC(O)C(Cc1ccc(OC(=O)CCS(=O)(=O)O)cc1)NC(=O)OCc1ccccc1] |
| 211 | 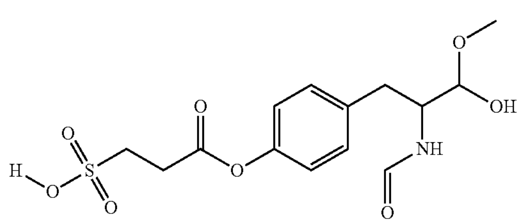 [SMILES: COC(O)C(Cc1ccc(OC(=O)CCS(=O)(=O)O)cc1)NC=O] |
| 212 | 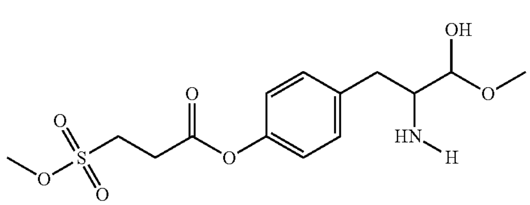 |

TABLE 1-continued

| # | Structure |
|---|---|
| 213 | 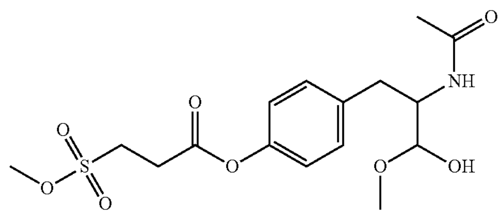 [SMILES: COC(O)C(Cc1ccc(OC(=O)CCS(=O)(=O)OC)cc1)NC(C)=O] |
| 214 | 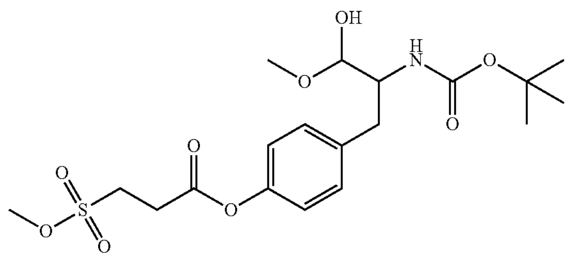 [SMILES: COC(O)C(Cc1ccc(OC(=O)CCS(=O)(=O)OC)cc1)NC(=O)OC(C)(C)C] |
| 215 | 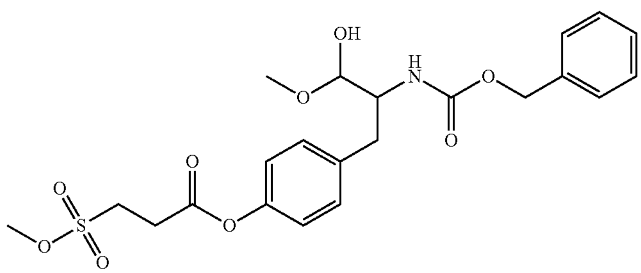 [SMILES: COC(O)C(Cc1ccc(OC(=O)CCS(=O)(=O)OC)cc1)NC(=O)OCc1ccccc1] |
| 216 | 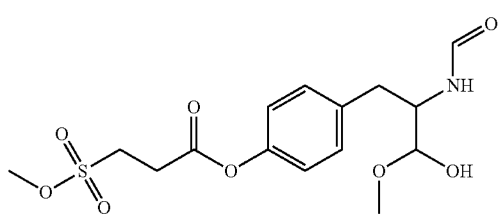 [SMILES: COC(O)C(Cc1ccc(OC(=O)CCS(=O)(=O)OC)cc1)NC=O] |
| 217 | 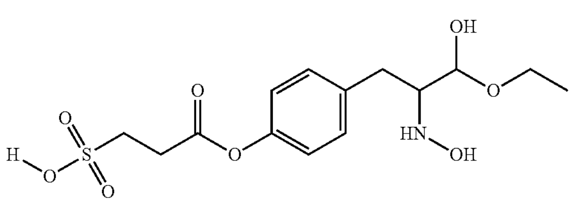 [SMILES: CCOC(O)C(Cc1ccc(OC(=O)CCS(=O)(=O)O)cc1)NO] |
| 218 | 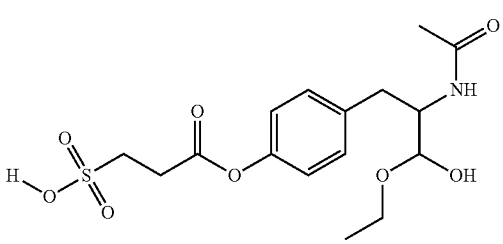 [SMILES: CCOC(O)C(Cc1ccc(OC(=O)CCS(=O)(=O)O)cc1)NC(C)=O] |

TABLE 1-continued

| # | Structure |
|---|---|
| 219 | 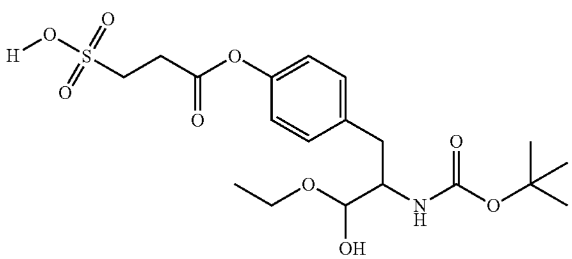 [SMILES: CCOC(O)C(Cc1ccc(OC(=O)CCS(=O)(=O)O)cc1)NC(=O)OC(C)(C)C] |
| 220 | 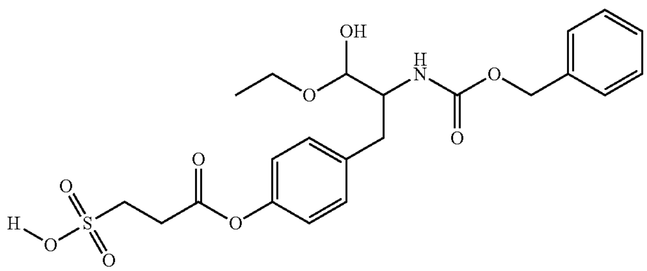 [SMILES: CCOC(O)C(Cc1ccc(OC(=O)CCS(=O)(=O)O)cc1)NC(=O)OCc1ccccc1] |
| 221 | 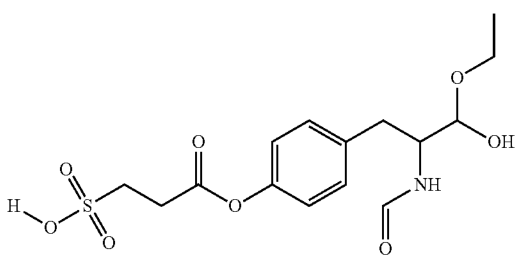 [SMILES: CCOC(O)C(Cc1ccc(OC(=O)CCS(=O)(=O)O)cc1)NC=O] |
| 222 | 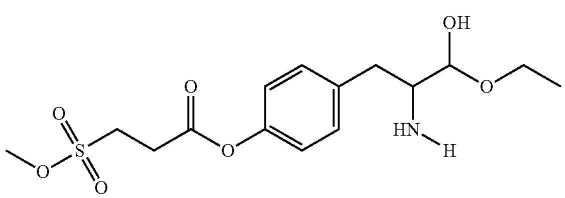 [SMILES: CCOC(O)C(N)Cc1ccc(OC(=O)CCS(=O)(=O)OC)cc1] |
| 223 | 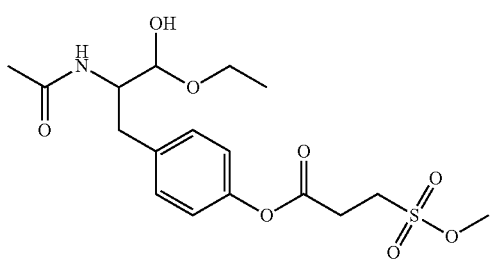 [SMILES: CCOC(O)C(Cc1ccc(OC(=O)CCS(=O)(=O)OC)cc1)NC(C)=O] |
| 224 | 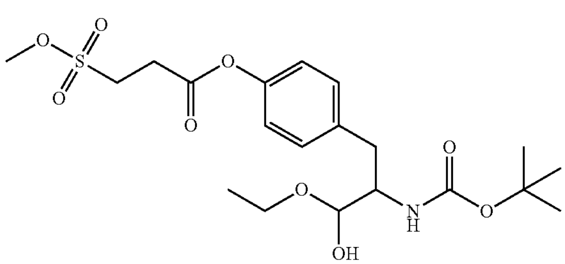 [SMILES: CCOC(O)C(Cc1ccc(OC(=O)CCS(=O)(=O)OC)cc1)NC(=O)OC(C)(C)C] |

TABLE 1-continued

| # | Structure |
|---|---|
| 225 | (structure: 4-substituted phenyl with CH2-CH(NHC(O)OCH2Ph)-CH(OH)(OEt) group; phenol O-C(O)-CH2CH2-S(O)2-OCH3) |
| 226 | (structure: 4-substituted phenyl with CH2-CH(NHC(O)H)-CH(OH)(OEt); phenol O-C(O)-CH2CH2-S(O)2-OCH3) |
| 227 | methyl 3-sulfopropanoate (CH3O-C(O)-CH2CH2-SO3H) |
| 228 | ethyl 3-sulfopropanoate |
| 229 | isobutyl 3-sulfopropanoate |
| 230 | propyl 3-sulfopropanoate |
| 231 | isopropyl 3-sulfopropanoate |
| 232 | butyl 3-sulfopropanoate |
| 233 | sec-butyl 3-sulfopropanoate |
| 234 | CH3-(CH2)16-O-C(O)-CH2CH2-SO3H |

TABLE 1-continued

| # | Structure |
|---|---|
| 235 | CH₃(CH₂)₉-O-C(=O)-CH₂CH₂-S(=O)₂-OH |

4. Formulation and Administration

The compounds of the methods described herein can be formulated as pharmaceutical compositions and administered to a subject, such as a human. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Liquid dosage forms, injectable preparations, solid dispersion forms, and dosage forms for topical or transdermal administration of a compound are included herein. In one aspect, administration is orally.

Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Methods of administration can use an amount and a route of administration effective for treating or lessening the severity of a disease described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. For example, provided compounds may be formulated such that a dosage of between 0.01-100 mg/kg body weight/day of the compound can be administered to a patient receiving these compositions. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

EXEMPLIFICATION

1. Methods

Human CSF Samples Collection and Processing

Individual CSF samples were obtained from 64 male and female subjects with cognitive impairment (MMSE range of 15-30) due to a variety of neurogenerative diseases (the descriptive characteristics are summarized in Table 1). These patients were referred to the Cognitive Center at the Department of Neurology, Charles University, 2nd Medical faculty and Motol University Hospital, Prague Czech Republic. The 64 samples were obtained from patients that were clinically diagnosed with the following conditions: Alzheimer's dementia (AD dementia; n=14), Mild cognitive impairment due to AD (MCI due to AD, n=20), mixed dementia (n=3), Lewy body disease (LBD; n=1), frontotemporal lobar degeneration (FTLD; n=18), mild cognitive impairment of other etiology (MCI other; n=7) and progressive supranuclear palsy (n=3). Vascular disease was considered when confluent vascular changes on MRI were present (Fazekas scale 2 and 3). 12 ml of CSF was withdrawn by lumbar puncture in supine position between vertebral body L3-L5 using atraumatic needle. The lumbar puncture was done between 8 am and 11 am and effectuated immediately after serum sample collection. CSF was transferred to the CSF lab, located at the same floor where spinning during 5 minutes at 2000 RPM at room temperature was done. After centrifugation, the CSF was aliquoted using 0.5 ml tubes and stored immediately at −80° C. Only polypropylene tubes were used for CSF withdrawal and storage. Processing time between CSF withdrawal, spinning and freezing was standardized and in total did not exceed 45 minutes.

The samples were withdrawn from the freezer and shipped on dry ice to Nextcea Inc (Woburn, MA) and stored in a freezer set to maintain −80° C. after receipt. The CSF collection and storage were carried out after subjects signed an informed consent in accordance with the ethical guidelines in the Czech Republic and good clinical practice, and according to the widely recognized consensus protocol for the standardization of CSF collection and biobanking (Viola et al., Amyloid 0 oligomers in Alzheimer's disease pathogenesis, treatment, and diagnosis. Acta Neuropathol 2015; 129:183-206; and Vanderstichele et al. Standardization of preanalytical aspects of cerebrospinal fluid biomarker testing for Alzheimer's disease diagnosis: A consensus paper from the Alzheimer's Biomarkers Standardization Initiative. Alzheimers Dement 2012; 8(1):65-73). Commercial ELISA kits (Innogenetics NV, Ghent, Belgium) were used for dementia biomarker analyses (Aβ1-42, tau protein, and phospho-tau), and cut off values derived from a validation study were used. CSF concentrations of 3-SPA were also quantified in 12 patients receiving the 150 mg BID dose of tramiprosate at Week 78 of the Phase 3 North American AD trial.

Identification and Quantitation of 3-SPA in Human CSF by LC-MS/MS

The CSF sample analysis was performed by Nextcea, using LC-MS and LC-MS/MS methods. A total of 64 human CSF samples were received at Nextcea for analysis.

Derivatization and LC-MS/MS Method

Figure 7:
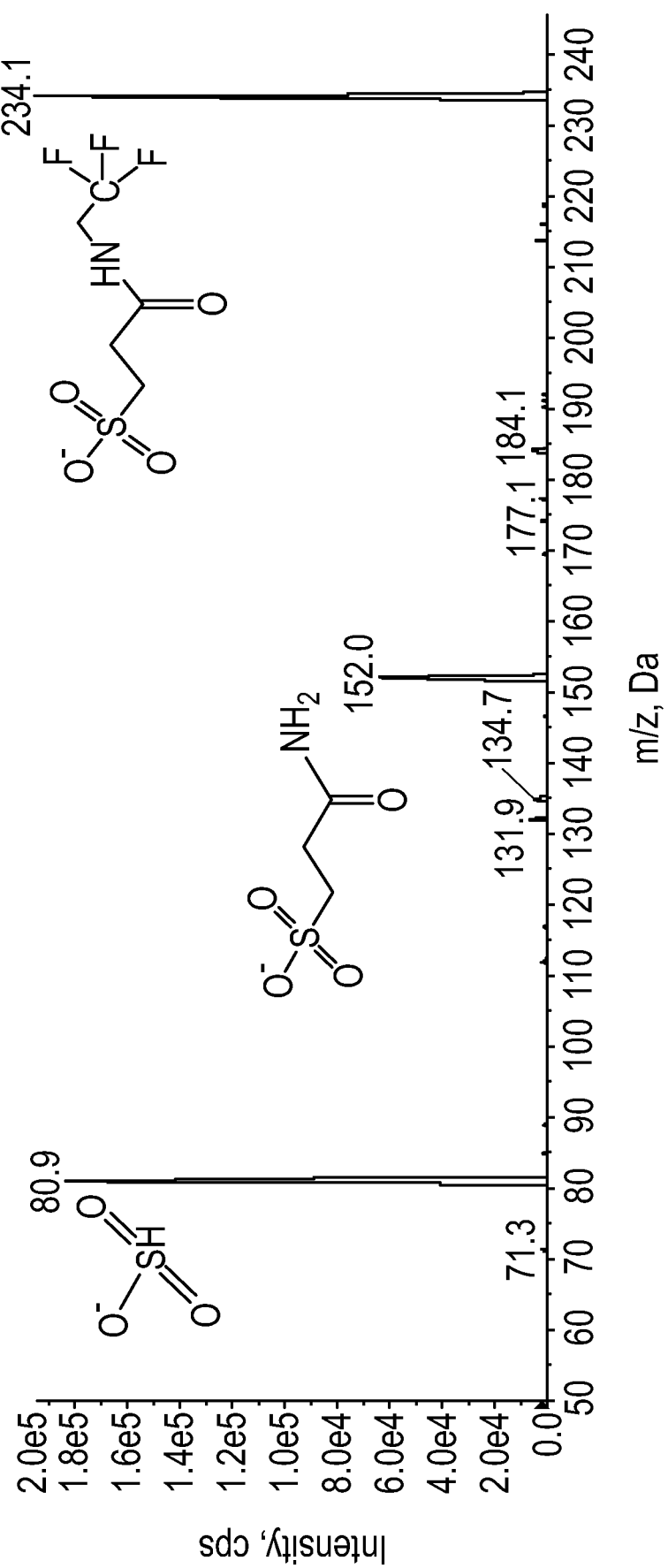
FIG. 7 represents the LC-MS/MS spectra of the authentic 3-SPA reference standard (derivatized with EDC and TFEA).
Figure 8:
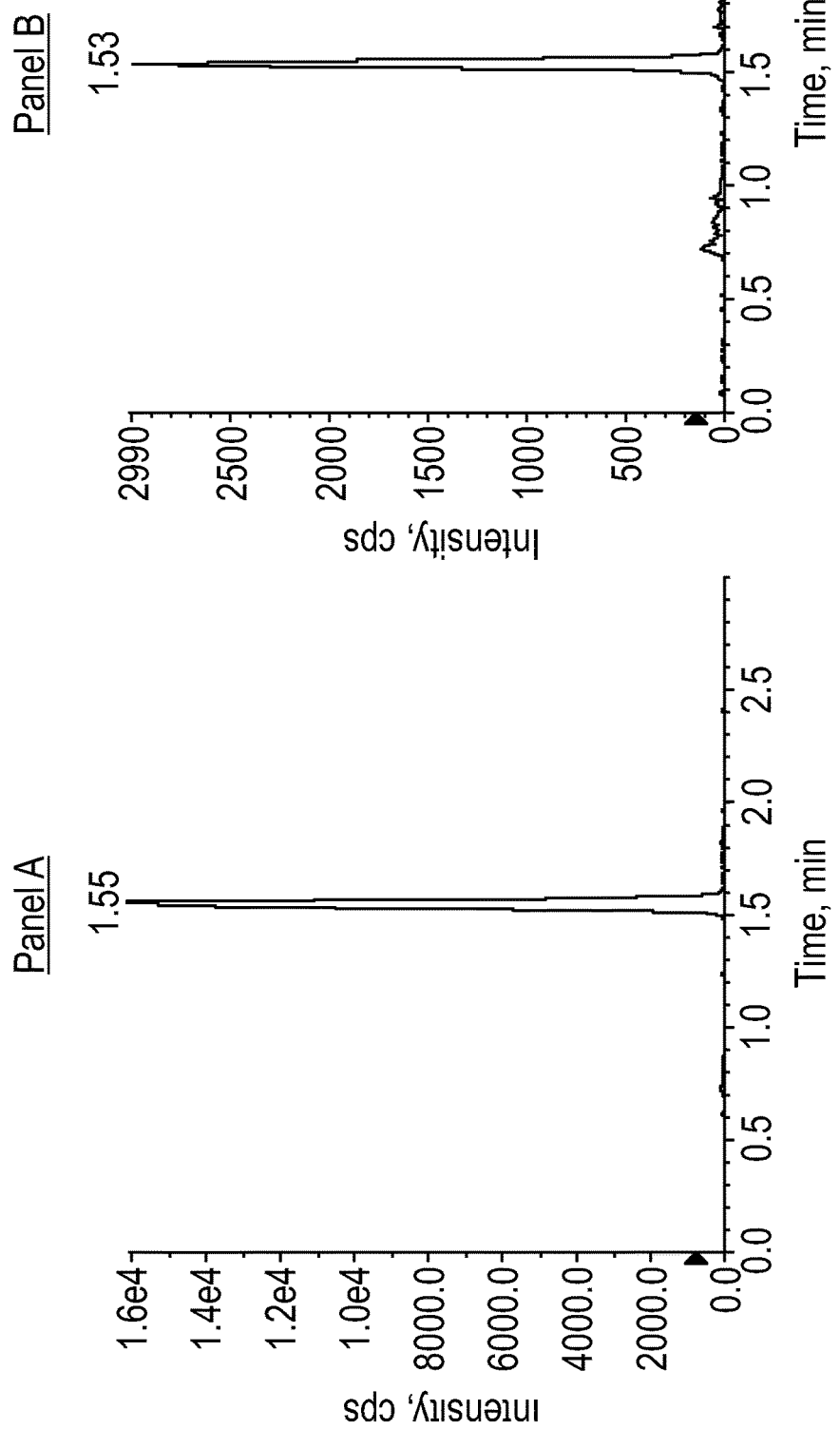
FIG. 8 Panel A represents the LC-MS/MS chromatograms for 3-SPA standard.

The 3-SPA reference material and human CSF samples were mixed with N-ethyl-N'-(3-dimethylaminopropyl) carbodiimide (EDC) and 2,2,2-trifluro ethylamine (TFEA). The samples were vortexed and reacted at room temperature for 30 minutes. The reactions were centrifuged at 4500 rpm for 5 minutes. The supernatant was transferred to a new plate for analysis. 3-SPA was identified and characterized using LC-MS and LC-MS/MS. Injections were made onto a Thermo Scientific AQUASIL 5 µm, 50×2.1 mm column using a Shimadzu autosampler and UPLC pump. Mobile phase A was 0.1% trifluoroacetic acid in water (v/v). Mobile phase B was 0.1% formic acid in 90/10 acetonitrile/water (v/v). The flow rate was 0.35 mL/min. The total running time per sample was 4 min. An API 6500 triple quadrupole mass spectrometer was used for detection. Data were acquired in negative LC-MS and LC-MS/MS modes. Representative chromatograms of 3-SPA in crude native material and human CSF derivatized with EDC and TFEA are shown in FIG. 7, FIG. 8 Panel A, and FIG. 8 Panel B. LC-MS and LC-MS/MS data were acquired using Analyst software (AB Sciex, Foster City, CA). LOQ for the LC-MS/MS method was 0.1 ng/ml with a dynamic range of 0.1 to 1000 ng/ml (r=0.99688 and % CV 5.8%±2.0; data on file). 3-SPA was identified in human CSF by matching the chromatographic retention time and by co-elution of the LC-MS/MS transition ions to the authentic 3-SPA reference standard (synthesized by Paraza Pharma, Montreal, Canada).

3-SPA Molecular Modeling and Molecular Dynamics Simulations

All molecular modeling was performed using the Schrödinger suite (Schrödinger Suite, 2015-3; Schrödinger, LLC, New York, NY). Molecular dynamics simulations were run using Desmond. See Vanderstichele et al. Standardization of preanalytical aspects of cerebrospinal fluid biomarker testing for Alzheimer's disease diagnosis: A consensus paper from the Alzheimer's Biomarkers Standardization Initiative. Alzheimers Dement 2012; 8(1):65-73. The simulations were run on GeForce GTX Titan Black GPU (graphics processing unit) cards. The OPLS 3.0 (Optimized Potential for Liquid Simulations) force field (Hort et al., The liquor tau protein and beta amyloid in Alzheimer's disease. Cesk Slov Neurol N 2007; 70(1):30-36) was used to model all interactions, and the SPC model was used for waters. The 1IYT Aβ42 NMR structure from the Protein Data Bank (PDB) was used as a starting point for molecular dynamics simulations. This structure is primarily alpha helical and is representative of the peptide in an apolar environment. A 20 Angstrom box of water or a mixed solvent box of 1% 3-SPA in water was added around the peptide using Schrödinger system setup tools. Ions were added to neutralize the charge of the entire system. Simulations were equilibrated and run under NPT conditions (constant number (N) pressure (P) and temperature (T) with periodic boundary conditions. The Nose-Hoover Thermostat and Martina-Tobias-Klein barostat were used to control temperature and pressure, respectively. Simulations were run in replicates of 3 for 100 nanoseconds each, and the results were compiled for analysis. Principal component analysis was performed using ProDy (Shivakumar et al., Improving the Prediction of Absolute Solvation Free Energies Using the Next Generation OPLS Force Field. J. Chem. Theory Comput 2012; 8:2553-8) and plotted using custom python scripts.

Ion Mobility Mass Spectrometry (IMS MS)

The conditions used for mass spectrometry, using a Waters Synapt G2-S, were as follows: positive polarity in sensitivity mode, capillary=2.5 kV, nebulizer=2 mbar, source temperature=80° C., desolvation temperature=60° C., sample cone setting=35 V, source offset setting=60 V, and mass range=500 to 4000 m/z. These conditions were maintained throughout the study to ensure consistency of the data and to avoid influencing the detection of oligomers due to preferential ionization conditions.

Samples were directly infused into the mass spectrometer at a flow rate of 10 µL/min using a Protea PM-1000 Syringe Pump and Hamilton 1 mL Syringe. The data acquisition of the amyloid peptide was performed using a Waters Synapt G2-S quadrupole time of flight mass spectrometer (Q-TOF MS) with traveling wave ion mobility (Waters Corp., Milford, MA). The data were acquired using the systems sensitivity mode to allow for the detection of the less abundant oligomers. Samples were infused at room temperature. The IMS MS studies were conducted at Protea, Inc. (Morgantown, WV).

Sample Preparation 1 mg of recombinant human Aβ42 peptide from BioLegend (99% purity, cat #843801) was reconstituted in 200 µL of Fisher Optima LC/MS grade water (cat #W6-1) and vortexed vigorously for 2 minutes to solubilize the peptide creating a 5 mg/mL solution. Samples were then diluted to a final concentration of 22 pmol/µL prior to incubation. The sample mixtures were then incubated at room temperature for 0, 4 and 24 hours. After the acquisition of incubated samples was completed, the raw data were analyzed using the Waters MassLynx v2.4 suite with DriftScover v2.7 to visualize drift times for the peptide.

Aβ42 Species Characterization

Aβ42 species characterization using IMS MS was performed by direct infusion at 22 pmol/µL in water. The peptide was prepared in water to maintain the native state conformation of the peptide and ion mobility data acquisition was performed to detect and characterize the conformational changes of the native state monomer and any oligomers that may have formed during the incubation.

3-SPA IMS MS Binding Study

The data acquisition for Aβ42 peptide was performed using a Waters Synapt G2-S quadrupole time of flight mass spectrometer (Q-TOF MS) with traveling wave ion mobility (Waters Corp., Milford, MA). The data were acquired using the systems sensitivity mode to allow for the detection of the less abundant oligomers. Samples were infused at room temperature as above.

1 mg of 3-SPA was reconstituted in 1 mL of Fisher Optima LC/MS grade water (cat #W6-1) and vortexed vigorously for 2 minutes until completely dissolved. The sample was then diluted to create 220 pmol/µL, and 22,000 pmol/µL solutions to perform a 100-fold, and 1,000-fold molar excess for the binding experiments with Aβ42 peptide.

1 mg of recombinant human Aβ42 peptide was reconstituted in 200 µL of Fisher Optima LC/MS grade water and vortexed vigorously to solubilize to a 5 mg/mL solution. Samples were then diluted to their final concentrations prior to incubation. The sample mixtures were incubated at room temperature for 0, 4 and 24 hours, followed by analysis as described above.

Pharmacokinetics, Oral Absorption and Brain Exposure of 3-SPA in Sprague-Dawley (SD) Rats The oral and iv pharmacokinetics of 3-SPA was evaluated in male Sprague-Dawley fasted rats at a dose of 30 mg/kg and 10 mg/kg respectively (n=3 per groups). Animals were housed in a standard facility, with water and food was provided ad libitum to the experiment. 3-SPA was dissolved in saline, was administered orally by gavage and intravenously as a bolus. Serial blood samples (approximately 1.0 mL each) were collected from each animal at 0.25, 0.5, 1, 2, 4, 8 and 24 hours after dosing into tubes containing K2EDTA and processed for plasma by centrifugation. Plasma samples were stored at −80° C. until bioanalyses.

A separate group of animals was dosed orally at 30 mg/kg and terminal brain, CSF and plasma samples were collected at 1, 2, 6, and 24 hr (3 animals for each time point) for bioanalyses of 3-SPA in brain and CSF, and to estimate brain penetration relative to plasma concentrations. The in-life study was performed at Agilux Laboratories (Worcester, MA) following quality standards in line with Good Laboratory Practice. Bioanalyses of rat plasma, CSF and brain was preformed using LC-MS/MS at Nextcea. Prior to processing rat brains for bioanalysis, the brains were perfused to remove pooled blood. Pharmacokinetic data analyses were conducted using Winnonlin Professional v5.0.1 (Pharsight, Mountain View, CA).

2. Results

Figure 2:
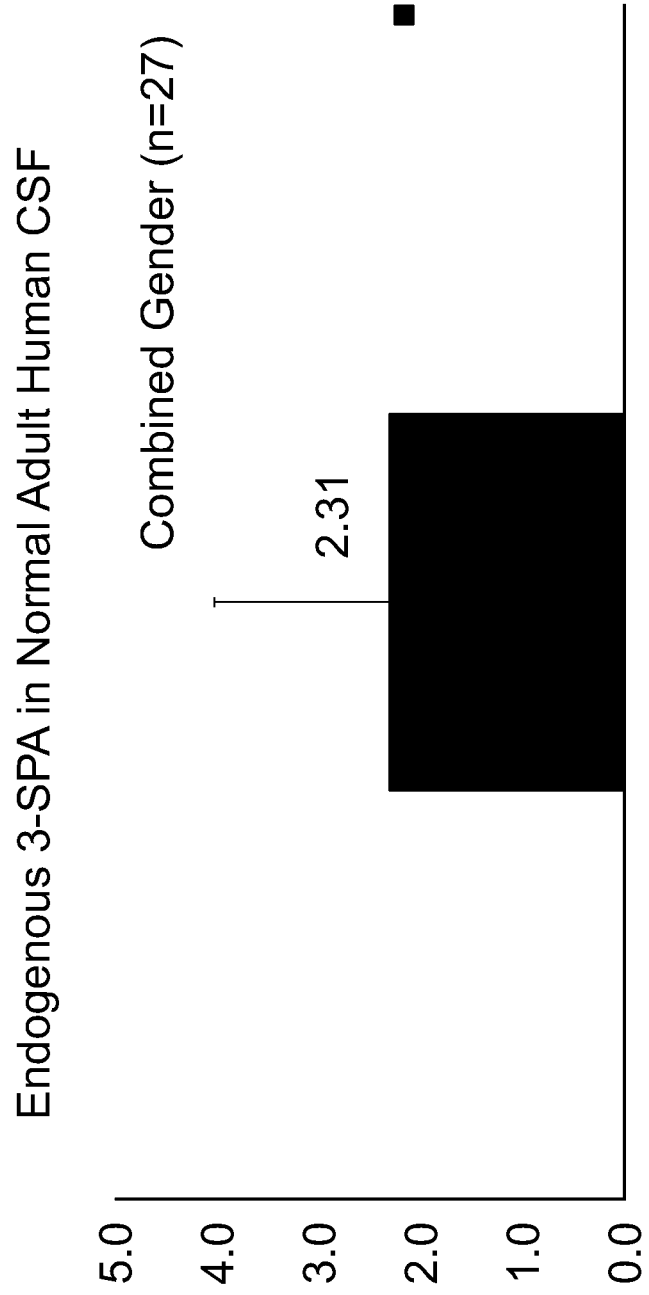
FIG. 2 is a graph showing the concentration (ng/ml) of 3-SPA present in human cerebrospinal fluid (CSF) of drug-naïve subjects who have not been diagnosed with AD.

Identification and Quantitation of 3-SPA in CSF of Drug Naïve Subjects and Tramiprosate-Treated AD Patients 3-SPA was identified and quantitated in human CSF by LC-MS/MS. The samples were derivatized with EDC and TFEA before analysis. LC-MS/MS transition ions were selected for monitoring based on 2-[(2,2,2-trifluoroethyl)carbamoyl]ethane-1-sulfonic acid, the product ion spectra of the derivatized 3-SPA reference standard. The [M-H]− of 3-SPA was detected in human CSF at m/z 234.1 at retention time 1.55 min. Structural match of 3-SPA in human CSF with authentic sample as standard was performed by matching the molecular peak of the acid as well as the molecular peaks of the 2-[(2,2,2-trifluoroethyl)-carbamoyl]ethane-1-sulfonic acid derivative including the MS-MS fragmentation pattern by monitoring two LC-MS/MS transition ions. The transition ions and retention time of 3-sulfopropanoic acid in human CSF matched with the authentic 3-sulfopropanoic acid reference standard. The transition ions of the molecular peak of the diacid (234.1/80.9) was selected for quantitation. The LLOQ of the LC-MS/MS assay was 0.1 ng/mL for 3-SPA. The concentrations of 3-SPA in human CSF are provided in Table 1. In a separate analysis, the presence of 3-SPA was also confirmed by LC-MS/MS in drug naïve samples of human CSF obtained from Bioreclamation, Westbury, NY (n=27 and n=88 respectively). See FIG. 2

TABLE 1

Concentrations of 3-SPA in human CSF in drug naïve patients with memory deficits

| Descriptive Statistics of patients with memory deficits | Concentration of 3-SPA in CSF ng/ml (nM) Combined Gender | Concentration of 3-SPA in CSF ng/ml (nM) Male | Concentration of 3-SPA in CSF ng/ml (nM) Female |
|---|---|---|---|
| n | 64 | 27 | 37 |
| Age | 68.6 ± 8.5 yr | 69.0 ± 8.7 yr | 68.1 ± 8.5 yr |
| Clinical diagnosis-n* | AD-14 MCI due to AD-20 MCI (other)-7 FTLD-18 Other- | AD-14 MCI due to AD-11 MCI (other)-2 FTLD-9 Other-1 | AD-10 MCI due to AD-9 MCI (other)-5 FTLD-9 Other-4 |
| MMSE range Mean ± SD | 25.0 ± 3.2 1.8 ± 0.7 (11.7 ± 4.3) | 25.4 ± 2.5 1.9 ± 0.6 (12.3 ± 3.9) | 24.6 ± 3.7 1.7 ± 3.7 (11.0 ± 4.5) |
| Median | 1.7 (11.0) | 1.7 (11.0) | 1.6 (10.3) |
| Minimum-maximum | 0.64-4.27 4.15-27.7) | 0.85-2.8 (5.6-18.5) | 0.64-4.27 (4.2-27.7) |

*AD-Alzheimer's disease, MCI-mild cognitive impairment, FTLD-frontotemporal lobular degeneration, Other-Lewy body disease, vascular dementia, mixed disease The levels of 3-SPA of in patients with a variety of cognition impairing diseases, including AD, ranged from 4.15 to 27.7 nM (0.64-4.27 ng/ml) (Table 1). When related to the CSF concentrations of Aβ42 monomers in AD patients (0.04 nM to 0.1 nM) (Bakan et al., ProDy: protein dynamics inferred from theory and experiments. Bioinformatics 2011; 27:1575-7; Shaw et al. Cerebrospinal fluid biomarker signature in Alzheimer's disease neuroimaging initiative subjects. Ann Neurol 2009; 65:403-13; Pannee et al. Reference measurement procedure for CSF Abeta1-42 and the CSF Abeta1-42/Abeta1-40 ratio—a crossvalidation study against Amyloid PET. J. Neurochem 2016; and Lambert et al. Diffusible, nonfibrillar ligands derived from A 1-42 are potent central nervous system neurotoxins. PNAS. 1998; 95:6448-53), there is an approximately 40-700 fold excess of 3-SPA over soluble Aβ42 monomers, which falls within the range where partial Aβ anti-oligomer aggregation activity may occur in some patients (Table 3). Furthermore, retrospective analyses of the CSF of a subset of patients from the tramiprosate Phase 3 trial were also evaluated for presence of 3-SPA, the primary metabolite of tramiprosate. Table 2 presents descriptive summaries of 3-SPA concentrations in CSF. The concentrations of metabolite were quantified in 6 patients for whom CSF samples at Week 78 were available. The mean CSF concentration of 3-SPA was 147 nM (range=114.3-235.8 nM), thus representing a 12.6-fold increase over levels observed in drug naïve patients.

TABLE 2

CSF concentrations (ng/mL) of 3-SPA at Week 78 in
North American Phase 3 tramiprosate trial

| Descriptive Statistics | 150 mg BID dose of tramiprosate, Week 78 of Phase 3 NA study (nM) |
|---|---|
| n | 6 |
| Mean ± SD | 22.3 ± 7.9 ng/ml (147 ± 51.3 nM) |
| Median | 19.3 ng/ml (127.5 nM) |
| Minimum-maximum | 17.3-35.7 ng/ml (114.3-235.8 nM) |

Anti-Aβ42 Oligomeric Activity of 3-SPA

Figure 3:
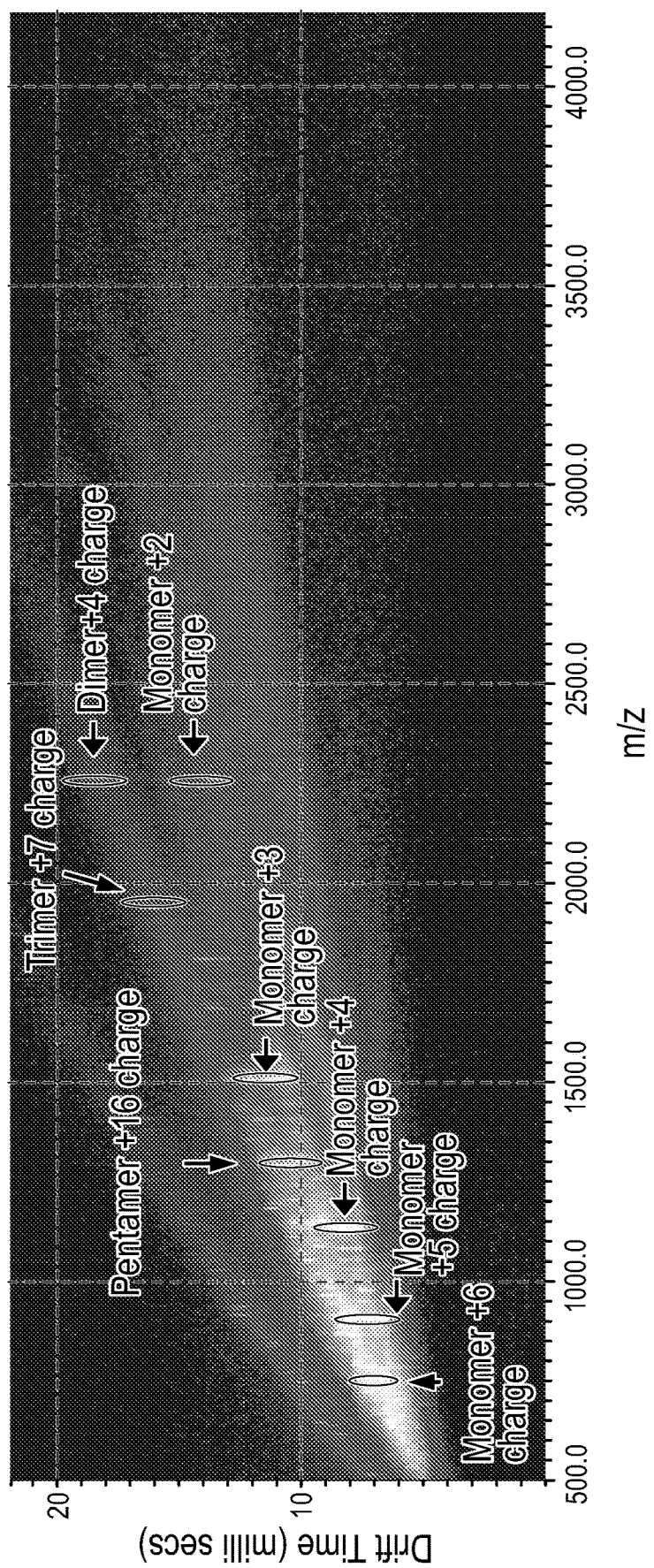
FIG. 3 depicts the ion-mobility spectrometry-mass spectrometry (IMS-MS) drift time as a function of mass/charge (m/z) after 4 hr incubation of Aβ42 with 3-SPA in ratio 1:1000 with the profile of Aβ42 oligomers. Detection of Aβ42 dimers, trimers and pentamers under these conditions reveals that 4 hours of in-vitro incubation was not sufficient for a complete inhibition of oligomer formation.
Figure 4:
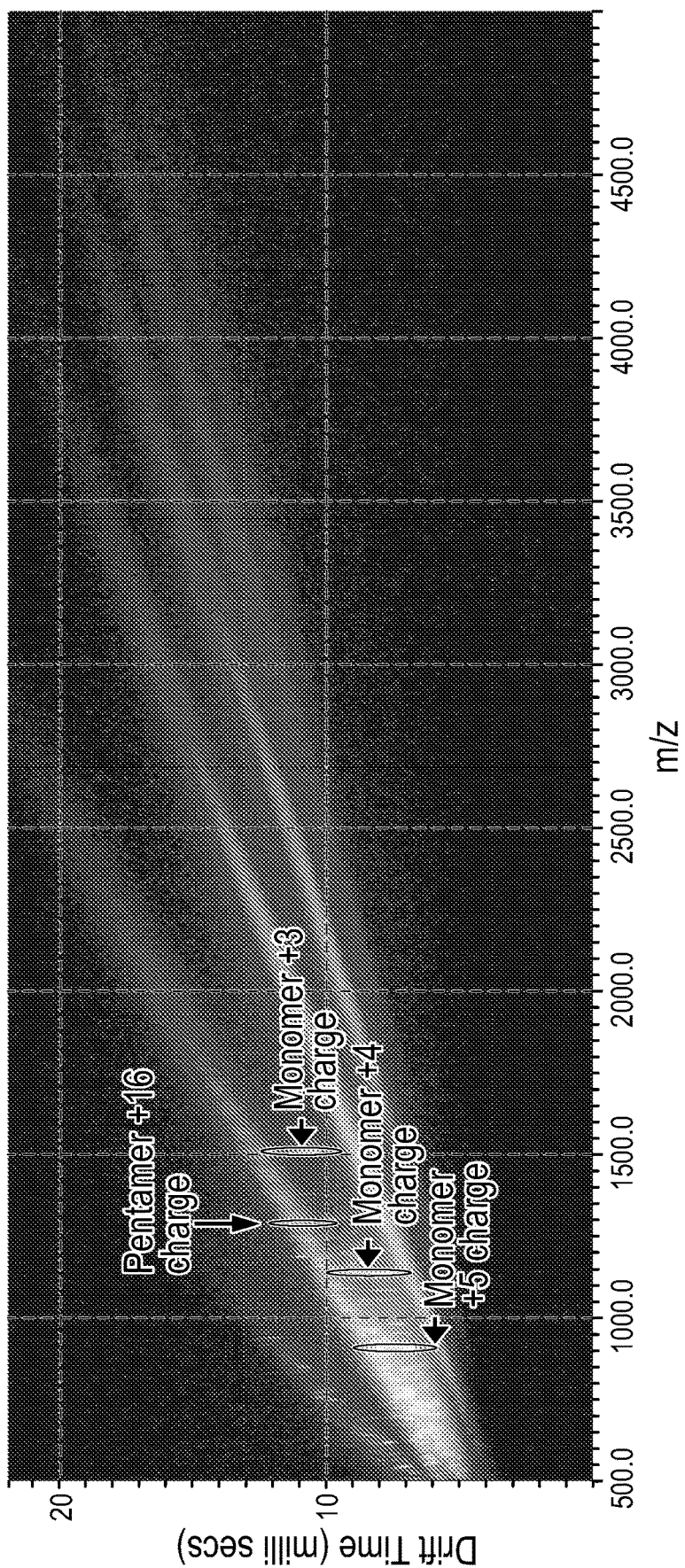
FIG. 4 depicts the ion-mobility spectrometry-mass spectrometry (IMS-MS) drift time as a function of mass/charge (m/z) after 24 hours of incubation shows the profile of Aβ42 oligomers with 1,000-fold excess of 3-SPA. Only pentamers were detected.

To address the high conformational flexibility of Aβ42 and to characterize its interaction with 3-SPA, we used ion mobility mass spectrometry (IMS), with a quadrupole time of flight mass spectrometer (Q-TOF MS) with traveling wave ion mobility. Resulting effect of modulation of Aβ conformational space is the prevention of oligomer formation. We have found not only concentration dependency but also time-dependency of this anti-Aβ42 oligomeric effect of 3-SPA as indicated in FIG. 3 and FIG. 4. The summary of the concentration excess dependency of 3-SPA over Aβ42 is presented in Table 3. 100- vs 1,000-fold molar excess of 3-SPA over Aβ42 results in a different sub-species profile of inhibition of Aβ42 oligomer formation. The activity is also compared with the same excess dependency of tramiprosate. Near complete prevention of formation of Aβ42 oligomers except for pentamers is shown for 3-SPA.

TABLE 3

Comparison of anti-Aβ42 oligomer activity of 3-SPA vs tramiprosate at 100:1 and 1,000:1 excess ratios of compound: protein

| Oligomer Species | Aβ42 alone | Tramiprosate 100:1 | 3-SPA 100:1 | Tramiprosate 1000:1 | 3-SPA 1000:1 |
|---|---|---|---|---|---|
| Dimer | Y | N | Y | N | N |
| Trimer | Y | Y | Y | N | N |
| Tetramer | Y | Y | Y | N | N |
| Pentamer | Y | Y | Y | N | Y |
| Hexamer | Y | Y | Y | N | N |
| Decamer | Y | N | N | N | N |

Y = yes, presence of oligomer species;
N = no presence of oligomer species.

Figure 5:
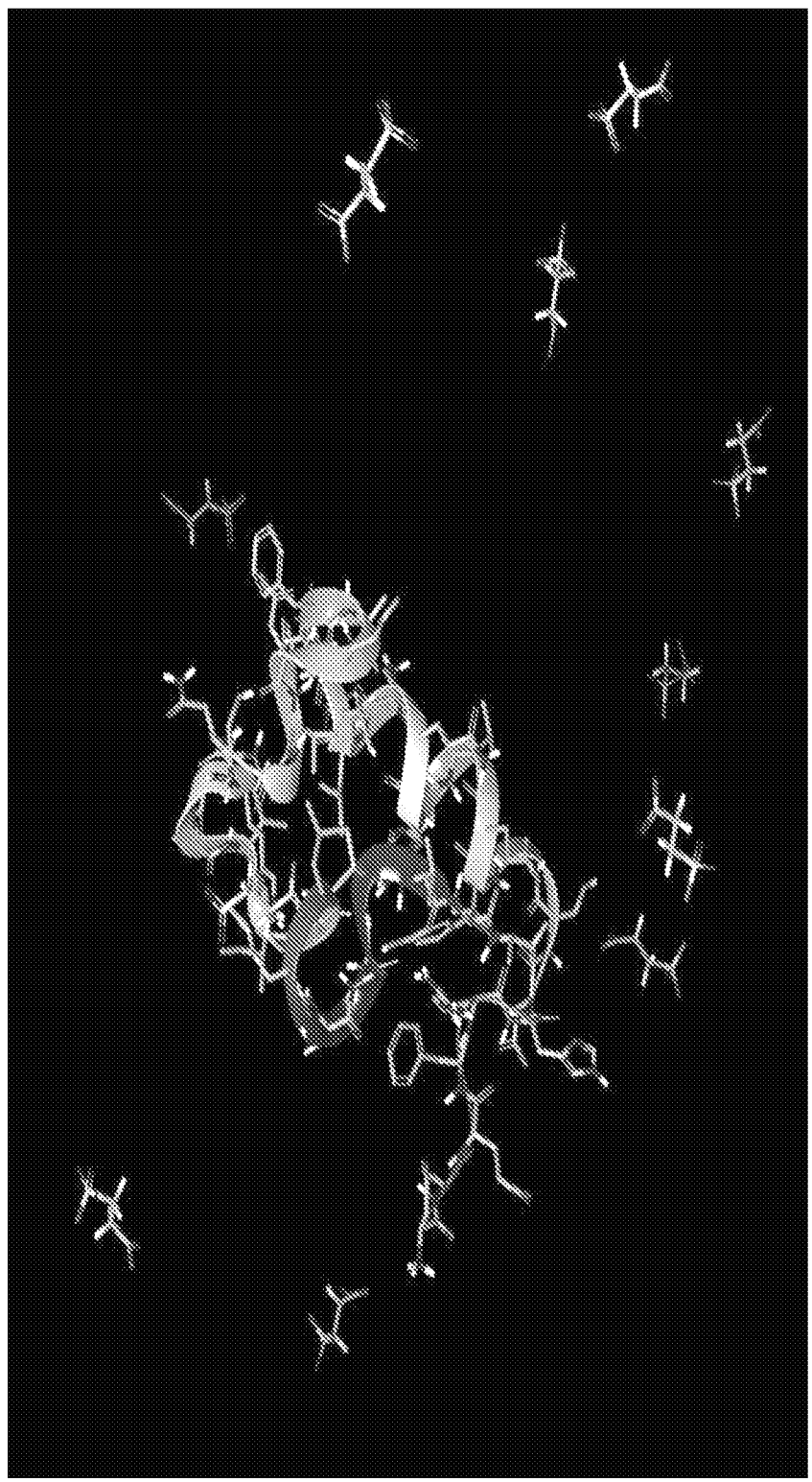
FIG. 5 is the representation of a molecular dynamics experiment showing semi-cyclic conformation of Aβ42 in the presence of 1,000:1 excess of 3-SPA. The functional result of 3-SPA is similar to the functional end results, i.e. inhibition of Aβ42 oligomer formation, found with tramiprosate (Kocis et al., Pharmacokinetic and Clinical Data. CNS Drugs 2017; 31:495-509).

While functional end results, i.e. inhibition of Aβ42 oligomer formation, are the same for both tramiprosate and its metabolite, 3-SPA, the conformational landscape of the process is not. 3-SPA as dianion under physiological conditions interacts with cations on amino acids side chains of Aβ42 (FIG. 5). These are protonated amino groups of Asp1, Lys16, Lys28, His13,14. At the same time repulsive forces of 3-SPA dianion and carboxylate groups of Aβ42 are at work. This interplay of ionic interactions contributes to significant conformational changes of Aβ42 monomer species.

Both ion mobility MS data and molecular dynamics (FIGS. 3, 4, 7, 8 Panel A, and 8 Panel B) display multi-ligand binding interaction of 3-SPA with Aβ42 monomers. 3-SPA interacts with Aβ42 via different ionic interactions than tramiprosate. Interestingly, although employing different ionic binding patterns, under the same conditions, data from IMS MS and molecular dynamics show qualitatively the same anti-Aβ42 oligomeric result from both compounds. Tramiprosate has shown complete inhibition of formation of Aβ42 oligomers after 24 hours in vitro, while 3-SPA has shown the same results with the exception of inhibition of formation of pentamers at the same time scale. However, a detailed time course investigation also shows a time-dependent course of oligomers inhibition. After 4 hours, 3-SPA inhibits the formation of oligomers with the exception of dimers, trimers and pentamers. After sustained 24 hours exposure, the only oligomeric species not inhibited were pentamers of Aβ42. These data suggest that the first anti-oligomeric effect of tramiprosate is followed by the second anti-oligomeric effect of tramiprosate metabolite 3-SPA.

Pharmacokinetics and Brain Penetration of Orally Administered 3-SPA in Rats

Figure 9:
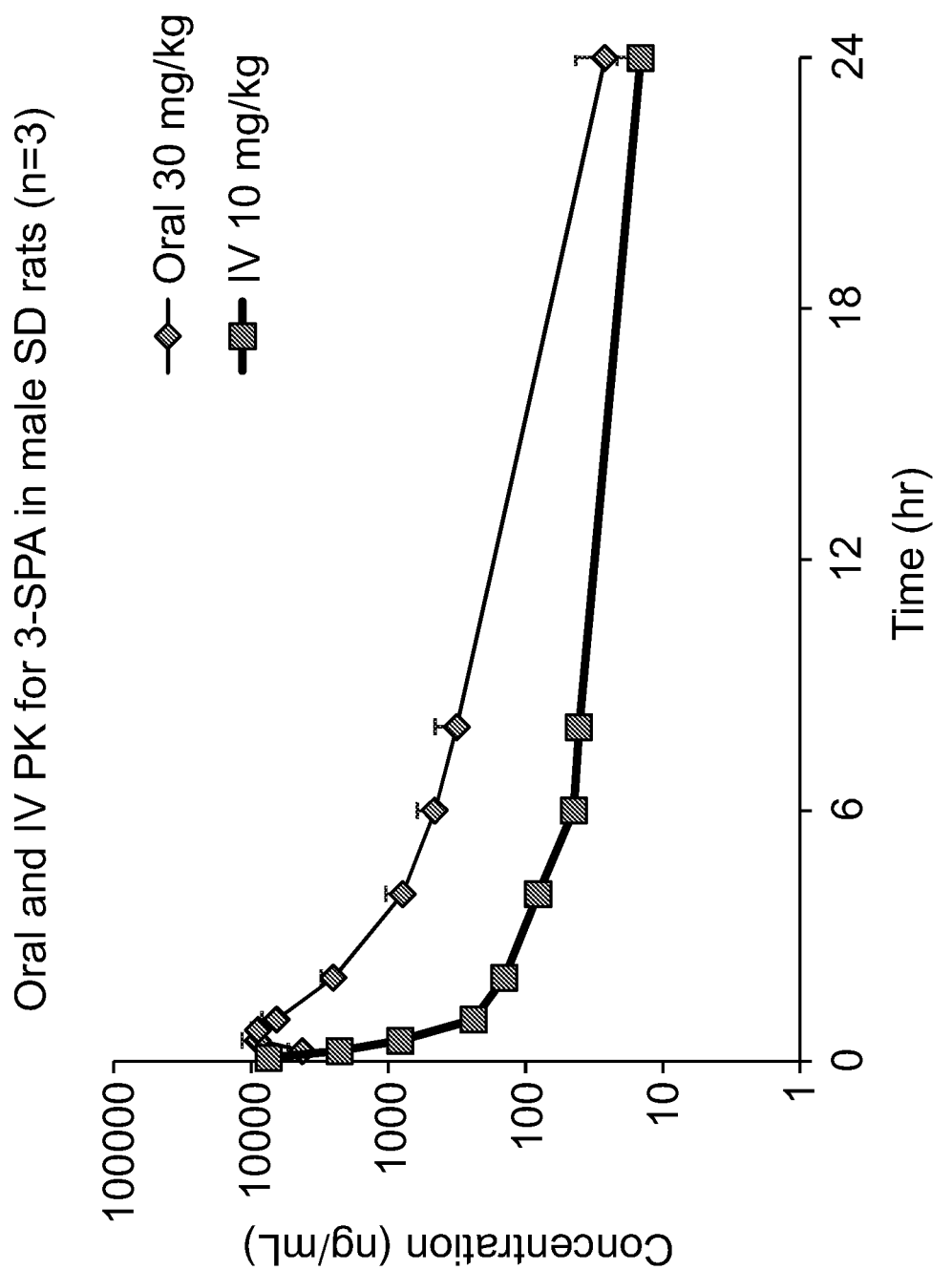
FIG. 9 shows the mean pharmacokinetic curves for single oral and iv doses of 3-SPA in male SD rats (30 mg/kg and 10 mg/kg, respectively; n=3). Data shown are mean±SD.
Figure 10:
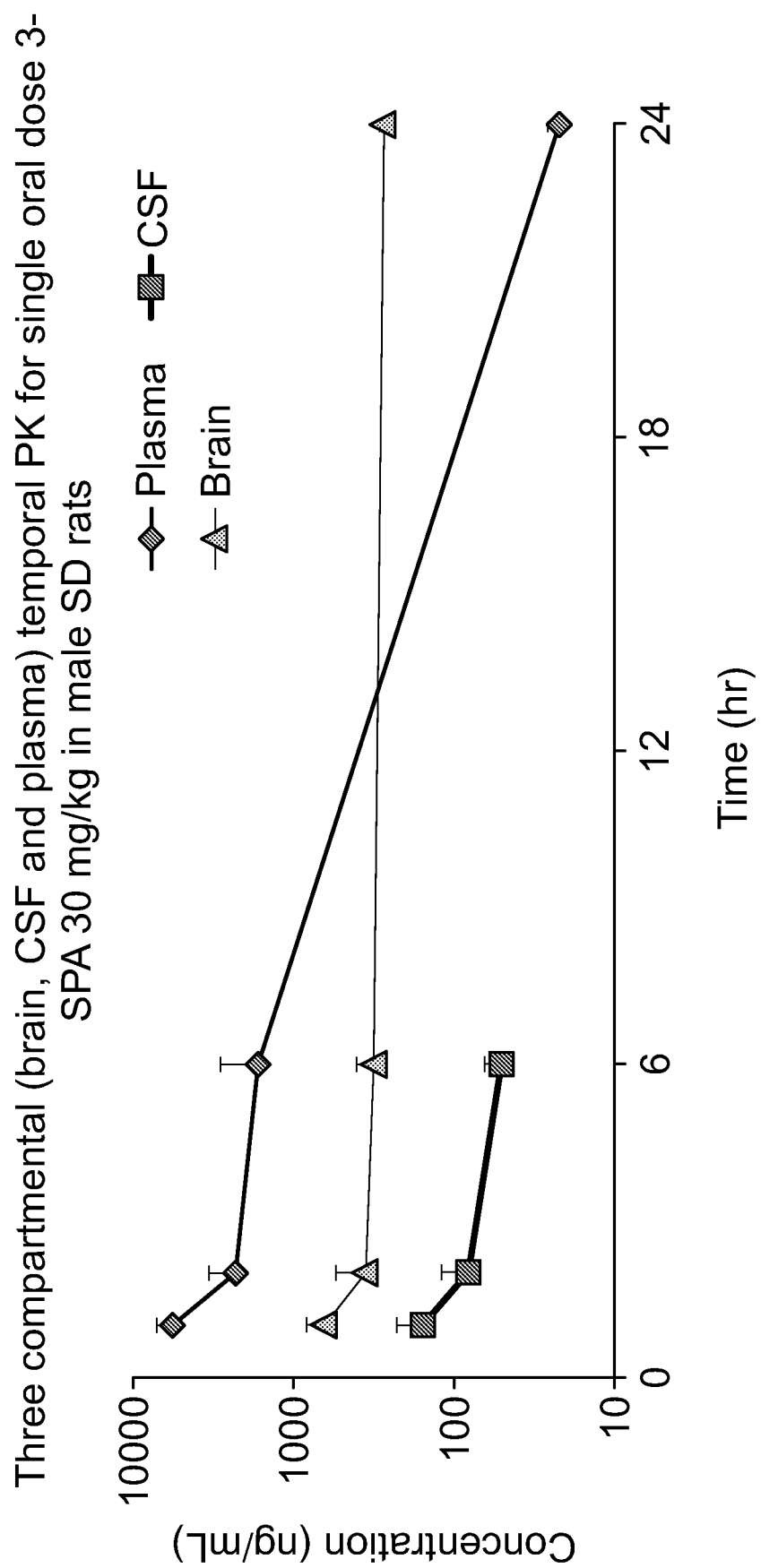
FIG. 10 shows the mean brain, CSF and plasma concentration time course of 3-SPA after a single oral dose of 30 mg/kg in male SD rats (n=3). Data shown are mean±SD.

The plasma concentration of a single dose of 3-SPA, dissolved in saline as a clear solution, administered orally and intravenously to rats at a dose level of 30 mg/kg and 10 mg/kg, respectively, are shown in FIG. 9. Brain, CSF and corresponding plasma levels after a single oral dose of dose of 30 mg/kg of 3-SPA at 1, 2, 6, and 24 hr are shown in FIG. 10. Mean PK curves were used for calculation of pharmacokinetic parameters. The resulting pharmacokinetic parameters, oral bioavailability and brain penetration of 3-SPA in rats are shown in Tables 4-6.

TABLE 4

Pharmacokinetic parameters of oral 3-SPA in male SD rats (n = 3)
Oral PK parameters (30 mg/kg)

| Parameter | Unit | Value |
|---|---|---|
| Lambda_z | l/h | 0.16 |
| t ½ | h | 4.40 |
| Tmax | h | 0.50 |
| Cmax | ng/ml | 8943 |
| AUC 0-t | ng/ml*h | 18894 |
| AUC 0-inf_obs | ng/ml*h | 19061 |

TABLE 5

Pharmacokinetic parameters of iv 3-SPA in male SD rats (n = 3)
IV PK parameters (10 mg/kg)

| Parameter | Unit | Value |
|---|---|---|
| t ½ | h | 10.99 |
| Tmax | h | 0.08 |
| Cmax | ng/ml | 7484 |
| C0 | ng/ml | 13599 |
| AUC 0-t | ng/ml*h | 3407 |
| AUC 0-inf_obs | ng/ml*h | 3638 |
| Vz_obs | L/kg | 43.6 |
| Cl_obs | L/kg/h | 2.7 |
| Vss_obs | L/kg | 12.9 |
| Oral Bioavailability | % | ~100 |

TABLE 6

Brain Penetration of Oral 3-SPA (30 mg/kg) in male SD rats

| PK Parameter | Unit | Plasma | Brain | CSF |
|---|---|---|---|---|
| t ½ | h | 3.03 | 64.07 | 3.56 |
| Cmax | ng/ml | 5714.6 | 649.8 | 159.2 |
| AUC 0-t | ng/ml*h | 30001.7 | 7586.5 | 463.6 |

TABLE 6-continued

Brain Penetration of Oral 3-SPA (30 mg/kg) in male SD rats

| PK Parameter | Unit | Plasma | Brain | CSF |
|---|---|---|---|---|
| AUC 0-inf_obs | ng/ml*h | 30099.2 | 33224.4 | 726.2 |
| Brain/Plasma (AUC %) | | | 25.3% | |
| CSF/brain AUC % | | | | 6.1% |

3. Preparation of Compounds of Formula I

General Synthesis of Alkyl Esters of 3-Sulfopropanoic-1-Alkyl Esters

The following reagents are added in this sequence: olefin (0.20 mmol), MeOH (2.0 mL), triethylamine (5.5 µL, 0.04 mmol) and 0.5 M aqueous sodium bisulfite (0.6 mL, 0.3 mmol) in a test tube equipped with a magnetic stirring bar. The reaction mixture is stirred at 22° C. for 14 hours.

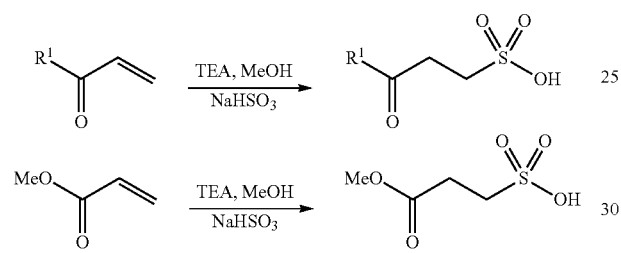

Alternatively, these alkyl esters can be prepared from beta-bromopropionic acid by reacting with $Na_2SO_3$ and the corresponding alcohol.

Alternative Procedure for Preparation of 3-sulfopropanoic-1-alkyl Esters

Reaction of 3-chloro-3-oxopropane-1-sulfonic acid with the corresponding $C_1$-$C_{20}$ alcohol in acetonitrile at room temperature affords the corresponding $C_1$-$C_{20}$ ester of 3-sulfopropanoic acid

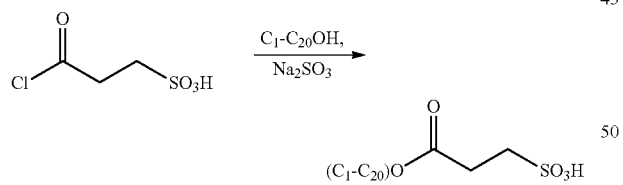

Preparation of Alpha-Sulfocarboxylic Acid Halide

The sulfocarboxylic acid chloride can be prepared by treating the sulfocarboxylic acid with a halogenating agent e.g. $SOCl_2$ in diethylether and a necessary amount of dimethylformamide for dissolution at 30° for 45 hrs.

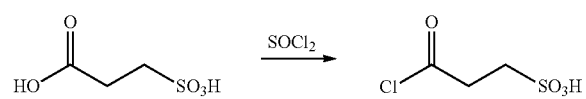

General Synthesis of 3-Sulfopropanoic Esters Derived from Amino Acids Linked Via Hydroxyl Functional Group in their Side Chain Reaction of 1 eq of N-protected amino acid or N-protected and carboxyl-derivatized amino acid with 1 eq of 3-chloro-3-oxopropane-1-sulfonic acid in organic solvent e.g. acetonitrile (with DMF as needed for solubilization or reactants) is mixed in room temperature. Depending on amino-protecting group triethyl amine or N-methypiperidine is added. Reaction is monitored until disappearance of starting amino acid. Reaction mixture is evaporated followed with typical work-up.

Synthesis of (2S)-2-[(tert-butoxycarbonyl)amino]-3-[(3-sulfopropanoyl)oxy]-propanoic Acid Reaction of 1 eq of Boc-L-serine with 1 eq of 3-chloro-3-oxopropane-1-sulfonic acid in organic solvent e.g. acetonitrile (with DMF as needed for solubilization or reactants) and N-methylpiperidine is mixed in room temperature. Reaction is monitored until disappearance of starting Boc-L-serine. Reaction mixture is evaporated with typical work-up affords (2S)-2-[(tert-butoxycarbonyl)amino]-3-[(3-sulfopropanoyl)oxy]propanoic acid.

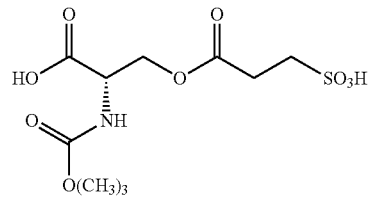

Preparation of (2S)-2-amino-3-[(3-sulfopropanoyl)oxy]propanoic Acid (2S)-2-[(tert-butoxycarbonyl)amino]-3-[(3-sulfopropanoyl)oxy]propanoic acid is deprotected in trifluoroacetic acid or in a mixture if dichloromethane with trifluoroacetic acid (1:1) in the presence of thioanizole for 30 min.

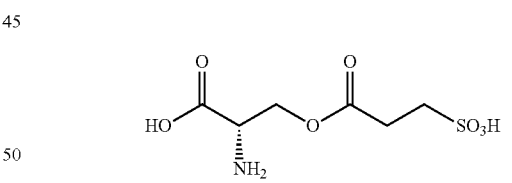

General Procedure for Synthesis of Compounds with Core Structure of 2-(carbamoylmethylcarbamoyl)ethanesulfonic acid, (3-sulfopropanamido)acetic Acid, [2-(3-sulfopropanamido)acetamido]acetic Acid, and 2-[(carbamoylmethylcarbamoyl)methylcarbamoyl]ethanesulfonic Acid 1 eq of appropriately N-protected and side-chain O-protected amino acid or amino acid derivative or N-protected and side-chain O-protected dipeptide or dipeptide derivative is added to 1 eq of 3-chloro-3-oxopropane-1-sulfonic acid in acetonitrile with DMF (depending on solubility of the reactants) and then 1 eq of terciary base e.g. trimethylamine or N-methylpiperidine is added. Reaction is run at room temperature and monitored until disappearance of starting amino acid or dipeptide component. Typical work-up affords the corresponding product.

The activity and/or pharmaceutical properties of the aforementioned compounds described herein can be obtained using biological and/or ADME assays know to those skilled in the art.

4. Discussion

From our studies we have discovered the presence of 3-SPA in human cerebrospinal fluid (CSF) of drug-naïve subjects. See e.g., FIG. 2. Also, as exemplified above (see e.g., Table 1), we have identified the presence of 3-SPA in the CSF of 64 naïve patients with cognitive defects. The mean 3-SPA concentration from the study was 11.7±4.3 nM. We have also shown that 3-SPA elicits anti-Aβ42 oligomeric effect in both a time and concentration dependent manner. See "Anti-Aβ42 oligomeric activity of 3-SPA" section presented above. We have further shown that that 3-SPA displays 100% oral bioavailability and 25% brain penetration indicating that 3-SPA is well absorbed and crosses the blood brain barrier. See Tables 4-6. Taken together, these data suggest that the higher CSF concentrations in human brain after oral administration of ALZ-801 or tramiprosate result from the penetration of the metabolite 3-SPA into the CNS.

Figure 6:
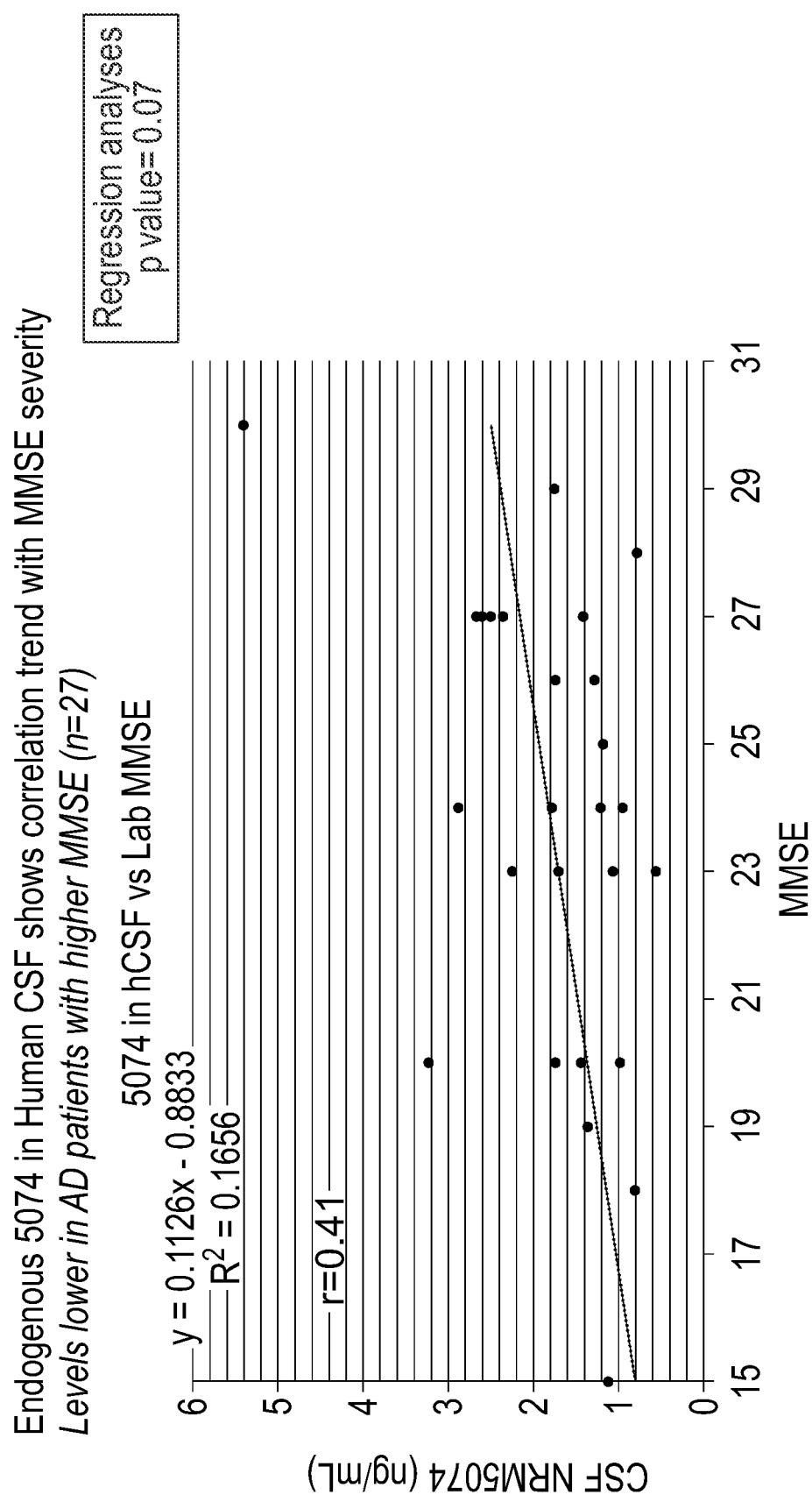
FIG. 6 illustrates an inverse correlation between 3-SPA levels in human CSF from a population of subjects having AD with varying MMSE scores (severity of AD).

We have also identified an inverse correlation between the concentration of 3-SPA in CSF and the severity of cognitive impairment. For example, as the severity of AD decreases, higher concentrations of 3-SPA were found in CSF. See FIG. 6. In contrast, as the severity of AD increases, lower concentrations of 3-SPA were found in CSF. See FIG. 6. This data suggests that the levels of 3-SPA in the brain play an important role in reducing the likelihood of, or delaying the onset of, disease progression.

From these findings, we hypothesize that increasing 3-SPA CSF levels can provide therapeutic benefit to subject suffering from AD. We also hypothesize that such an increase will provide additional benefit to AD subjects with the least cognitive impairment (i.e., MMSE=30) (a "baseline threshold level") and maintaining such elevated levels should protect those subjects from further cognitive decline or reduce the rate of cognitive decline as compared to a placebo treatment. Increasing 3-SPA CSF levels to above such baseline threshold level can be achieved by administering a compound of Formula I as described herein. This new therapeutic approach provides means for reducing amyloid beta oligomer neurotoxicity, and provides clinical routes for treating cognitive disorders such as AD.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) that may be cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method of treating a subject suffering from Alzheimer's disease, comprising the step of administering to the subject an effective amount of a compound of Formula I:

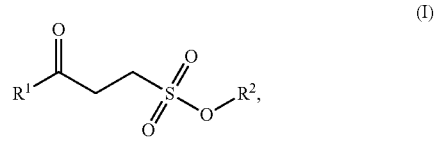

or a pharmaceutically acceptable salt thereof, wherein:
$R^1$ is selected from —O—$R^3$, —O—$R^4$—CH(NH$R^6$)—C(O)—$R^5$, and —[N($R^6$)—CH($R^7$)—C(O)]$_{1-2}$—$R^5$;
$R^2$ is selected from hydrogen, $R^3$, and $R^4$—CH(NH$R^6$)—C(O)—O—$R^5$;
each $R^3$ is independently selected from $C_1$-$C_{20}$ alkyl,-$C_2$-$C_{20}$ alkenyl,-$C_2$-$C_{20}$ alkynyl, -($C_0$-$C_{20}$ alkylene)-aryl,-($C_0$-$C_{20}$ alkylene)-carbocyclyl,-($C_0$-$C_{20}$ alkylene)-heterocyclyl,-($C_0$-$C_{20}$ alkylene)-heteroaryl,-($C_2$-$C_{20}$ alkenylene)-aryl,-($C_2$-$C_{20}$ alkenylene)-carbocyclyl,-($C_2$-$C_{20}$ alkenylene)-heterocyclyl,-($C_2$-$C_{20}$ alkenylene)-heteroaryl,-($C_2$-$C_{20}$ alkynylene)-aryl,-($C_2$-$C_{20}$ alkynylene)-carbocyclyl,-($C_2$-$C_{20}$ alkynylene)-heterocyclyl, and-($C_2$-$C_{20}$ alkynylene)-heteroaryl;
each $R^4$ is an independently selected from -CH(CH$_3$)-,-CH$_2$-,

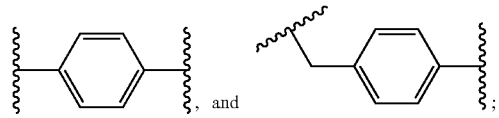 [SMILES: *c1ccc(*)cc1 ; *Cc1ccc(*)cc1]

, and ;

each $R^5$ is independently selected from —OH,—O—$C_1$-$C_4$ alkyl and —NH$_2$;
each $R^6$ is independently selected from hydrogen and —C(O)$R^8$;
$R^7$ is a side chain of an α-amino acid; and
each $R^8$ is independently selected from hydrogen, $C_1$-$C_4$ alkyl,—O—$C_1$-$C_4$ alkyl,—($C_1$-$C_4$ alkylene)-aryl, and ($C_1$-$C_4$ alkoxy)-aryl;
wherein:
each alkyl, alkylene, alkenyl, alkenylene, alkynyl or alkynylene portion of $R^3$ is optionally substituted with up to 6 substituents independently selected from halo,—OH,—O—($C_1$-$C_4$ alkyl),—O—($C_1$-$C_4$ haloalkyl), carbocyclyl, aryl, heterocyclyl, and heteroaryl;
each carbocyclyl, aryl, heterocyclyl, or heteroaryl portion of $R^3$ is optionally substituted with up to four substituents independently selected from halo,—OH,—O—($C_1$-$C_4$ alkyl),—O—($C_1$-$C_4$ haloalkyl), $C_1$-$C_{18}$ alkyl, $C_2$-$C_{18}$ alkenyl, and $C_2$-$C_{18}$ alkynyl, wherein the alkyl, alkenyl, or alkynyl portions of the $C_1$-$C_{18}$ alkyl, $C_2$-$C_{18}$ alkenyl, or $C_2$-$C_{18}$ alkynyl, respectively, are optionally substituted with up to six substituents independently selected from halo,-OH,-O-($C_1$-$C_4$ alkyl), and-O-($C_1$-$C_4$ haloalkyl);
$R^1$ comprises no more than 2 cyclic moieties; and
$R^2$ comprises no more than 2 cyclic moieties.

2. The method of claim 1, wherein $R^2$ is selected from hydrogen and $C_1$-$C_6$ alkyl.

3. The method of claim 1, wherein $R^2$ is selected from hydrogen and -CH$_3$.

4. The method of claim 1, wherein:
R$^1$ is selected from —O—R$^3$, —O—R$^4$—CH(NHR$^6$)—C(O)—R$^5$, and —O—R$^4$—CH(NHR$^6$)—CH(OH)—R$^5$; and
R$^3$ is C$_1$-C$_4$ alkyl.

5. The method of claim 1, wherein $R^6$ is selected from hydrogen, —C(O)H, —C(O)CH$_3$, —C(O)O—C(CH$_3$)$_3$, and —C(O)O—benzyl.

6. The method of claim 1, wherein $R^5$ is selected from —OH, —OCH$_3$, and —OCH$_2$CH$_3$.

7. The method of claim 1, wherein the subject is treated only after being determined to have an endogenous level of a compound of the formula:

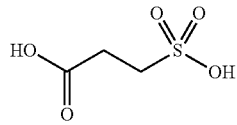

below a pre-determined baseline threshold prior to the treatment.

8. The method of claim 7, wherein the concentration of 3-SPA in the subject is the concentration of 3-SPA in the cerebrospinal fluid.

9. The method of claim 1, wherein the subject is administered a compound of Formula I only if the subject is ApoE4 heterozygous.

10. The method of claim 1, wherein the subject is administered a compound of Formula I only if the subject is ApoE4/4 homozygous.

11. The method of claim 1, wherein the subject is selected or administered a compound of Formula I only if the subject has a MMSE score of 22 to 28 prior to treatment.

12. The method of claim 1, wherein the subject is selected or administered a compound of Formula I only if the subject has a MMSE score of 22 to 26 prior to treatment.

13. The method of claim 1, wherein the pre-determined baseline threshold is defined as a 3-SPA concentration of less than 25 ng/ml.

14. The method of claim 1, wherein the pre-determined baseline threshold is defined as a 3-SPA concentration of between 6 ng/ml and 25 ng/ml.

15. The method of claim 1, wherein the pre-determined baseline threshold is defined as a 3-SPA concentration of less than 5 ng/ml.

16. The method of claim 1, wherein the pre-determined baseline threshold is defined as a 3-SPA concentration of 2 ng/ml to 4 ng/mL.

* * * * *